United States Patent
Silver et al.

(10) Patent No.: US 10,258,672 B2
(45) Date of Patent: Apr. 16, 2019

(54) COMPOSITIONS AND METHODS OF TREATING ROOT AVULSION INJURY

(71) Applicant: CASE WESTERN RESERVE UNIVERSITY, Cleveland, OH (US)

(72) Inventors: Jerry Silver, Cleveland, OH (US); Bradley T. Lang, Cleveland, OH (US); Jared M. Cregg, Cleveland, OH (US); Yi-Lan Weng, Cleveland, OH (US); Heng Li, Pok Fu Iam (HK); Wutian Wu, Pok Fu Lam (HK)

(73) Assignees: CASE WESTERN RESERVE UNIVERSITY, Cleveland, OH (US); THE UNIVERSITY OF HONG KONG, Hong Kong (HK)

(*) Notice: Subject to any disclaimer, the term of this patent is extended or adjusted under 35 U.S.C. 154(b) by 61 days.

(21) Appl. No.: 15/274,236

(22) Filed: Sep. 23, 2016

(65) Prior Publication Data
US 2017/0072026 A1   Mar. 16, 2017

Related U.S. Application Data

(63) Continuation-in-part of application No. 14/391,589, filed on Oct. 9, 2014, now Pat. No. 9,937,242.

(60) Provisional application No. 62/222,663, filed on Sep. 23, 2015, provisional application No. 62/222,578, filed on Sep. 23, 2015.

(51) Int. Cl.
*A61K 38/00* (2006.01)
*A61K 38/46* (2006.01)
*A61K 39/00* (2006.01)

(52) U.S. Cl.
CPC .......... *A61K 38/465* (2013.01); *A61K 38/005* (2013.01); *A61K 39/0011* (2013.01); *C12Y 301/03048* (2013.01); *A61K 2039/5158* (2013.01); *A61K 2039/55522* (2013.01); *C07K 2319/10* (2013.01)

(58) Field of Classification Search
None
See application file for complete search history.

(56) References Cited

U.S. PATENT DOCUMENTS

| | | |
|---|---|---|
| 2004/0138255 A1 | 7/2004 | Huang et al. |
| 2009/0042872 A1 | 2/2009 | Ryu et al. |
| 2009/0202544 A1 | 8/2009 | Sucio-Foca |
| 2012/0231014 A1 | 9/2012 | Flanagan |
| 2014/0045762 A1 | 2/2014 | Flanagan |

FOREIGN PATENT DOCUMENTS

| | | |
|---|---|---|
| WO | 02083182 A2 | 10/2002 |
| WO | 2009072726 A1 | 6/2009 |
| WO | 2012019086 A2 | 9/2012 |

OTHER PUBLICATIONS

Romeo-Guitart et al. "Boosted Regeneration and Reduced Denervated Muscle Atrophy by Neuro Heal in a Pre-clinical Model of Lumbar Root Avulsion with Delayed," Sci Rep. Sep. 20, 2017;7(1), p. 1-12 (Year: 2017).*
Koren, et al., "Inhibition of the protein tyrosine phosphatase PTP1B: Potential therapy for obesity, insulin resistance and type-2 diabetes mellitus", Best Practice and Research Clinical Endocrinology and Metabolism, vol. 21, No. 4, pp. 621-640, Dec. 31, 2007.
Aricescu, A. Radu, et al., "Heparan Sulfate Proteoglycans Are Ligands for Receptor Protein Tyrosine Phosphatase σ", Molecular and Cellular Biology, Mar. 2002, p. 1881-1892, vol. 22, No. 6.
Brown, Joshua M., et al., "A sulfated carbohydrate epitope inhibits axon regeneration after injury", PNAS, Mar. 27, 2012, vol. 109, No. 13, pp. 4768-4773.
Carey, D.J., et al. "Association of Cell Surface Heparan Sulfate Proteoglycans of Schwann Cells with Extracellular Matrix Proteins", J. Biol. Chem. 1990, 265:20627-20633.
Coles, Charlotte, et al. Proteoglycan-Specific Molecular Switch for RPTPσ Clustering and Neuronal Extension, Science. Apr. 22, 2011, 332(6028): 484-488.
Cortes, Mauricio, et al., "Sulfation if Chondroitin Sulfate Proteoglycans is necessary for proper Indian hedgehog signaling in the developing growth plate", Development 136, 1697-1706 (2009).
Dickendesher, Travis, L., "NgR1 and NgR3 are Receptors for Chondroitin Sulfate Proteoglycans", Nat. Neurosci.; 15(5): 703-712.
Fisher, Daniel, et al., "LAR is a functional receptor for CSPG Axon Growth Inhibitors", J. Neurosci. Oct. 5, 2011; 31(40):14051-14066.
Horn, Kevin, et al., "Another barrier to regeneration in the CNS: Activated macrophages induce extensive retraction of dystrophic axons through direct physical interactions", J. Neurosci. Sep. 17, 2008; 28(38):9330-9341.
Majeti, Ravindra, et al., "Dimerization-Induced Inhibition of Receptor Protein Tyrosine Phosphatase Function Through an Inhibitory Wedge", Science vol. 279, Jan. 2, 1998.
Shen, Yingjie, et al., "PTPσ is a Receptor for Chondroitin Sulfate Proteoglycan, an Inhibitor of Neural Regeneration", Science. Oct. 23, 2009; 326(5952: 592-596.
Tom, Veronica J., et al., "Studies in the Development and Behaviro of the Dystrophic Growth Cone, the Hallmark of Regeneration Failure, and an In Vitro Model of the Glial Scar and after Spinal Injury", The journal of Neuroscience, Jul. 21, 2004, 24(29):6531-6539.
Xie, Youmei, et al., "Protein-Tyrosine Phosphatase (PTP) Wedge Domain Peptides: A Novel Approach for Inhibition of PTP Function and Augmentation of Protein-Tyrosine Kinase Function", J. Biol. Chem. 2006, 281-16482-16492.

* cited by examiner

*Primary Examiner* — Christina Bradley
(74) *Attorney, Agent, or Firm* — Tarolli, Sundheim, Covell & Tummino LLP

(57) ABSTRACT

A method of treating root avulsion injury in a subject in need thereof includes administering to the subject a therapeutic agent that inhibits one or more of catalytic activity, signaling, and function of PTPσ.

7 Claims, 7 Drawing Sheets
Specification includes a Sequence Listing.

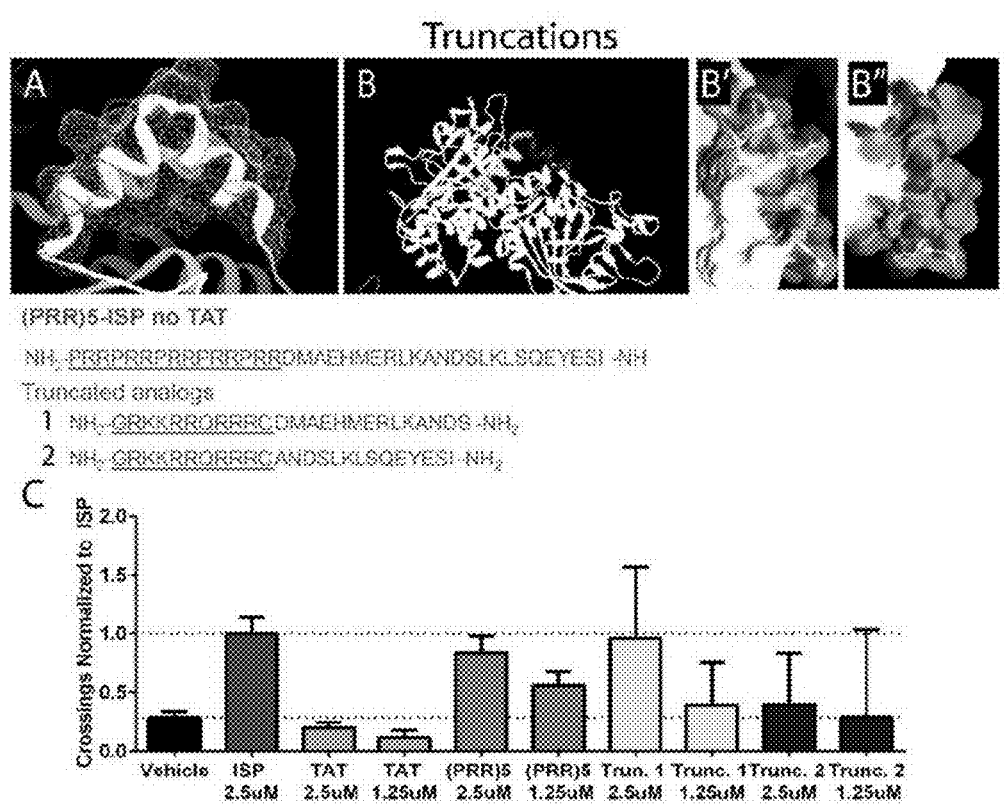
Figs. 7A-C

SEQUENCE LISTING

```
<160> NUMBER OF SEQ ID NOS: 63

<210> SEQ ID NO 1
<211> LENGTH: 22
<212> TYPE: PRT
<213> ORGANISM: Xenopus borealis

<400> SEQUENCE: 1

Asp Leu Ala Glu His Thr Glu His Leu Lys Ala Asn Asp Asn Leu Lys
1               5                   10                  15

Ser Gln Glu Tyr Glu Ser
            20

<210> SEQ ID NO 2
<211> LENGTH: 22
<212> TYPE: PRT
<213> ORGANISM: Anolis carolinensis

<400> SEQUENCE: 2

Asp His Thr Glu His Glu Leu Lys Ala Asn Asp Asn Leu Lys Leu Ser
1               5                   10                  15

Gln Glu Tyr Glu Ser Ile
            20

<210> SEQ ID NO 3
<211> LENGTH: 24
<212> TYPE: PRT
<213> ORGANISM: Danio rerio
```

```
<400> SEQUENCE: 3

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 4
<211> LENGTH: 24
<212> TYPE: PRT
<213> ORGANISM: Oreochromis aureus

<400> SEQUENCE: 4

Glu Leu Ala Glu His Thr Glu Leu Leu Lys Ala Asn Asp Asn Leu Lys
1               5                   10                  15

Leu Ser Gln Glu Tyr Glu Ser Ile
            20

<210> SEQ ID NO 5
<211> LENGTH: 24
<212> TYPE: PRT
<213> ORGANISM: Gallus gallus

<400> SEQUENCE: 5

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 6
<211> LENGTH: 24
<212> TYPE: PRT
<213> ORGANISM: Fringilla coelebs

<400> SEQUENCE: 6

Glu Leu Ala Glu His Thr Glu His Leu Lys Ala Asn Asp Asn Leu Lys
1               5                   10                  15

Leu Ser Gln Glu Tyr Glu Ser Ile
            20

<210> SEQ ID NO 7
<211> LENGTH: 24
<212> TYPE: PRT
<213> ORGANISM: Ornithorhynchus anatinus

<400> SEQUENCE: 7

Glu Leu Ala Glu His Thr Asp His Leu Lys Ala Asn Asp Asn Leu Lys
1               5                   10                  15

Leu Ser Gln Glu Tyr Glu Ser Ile
            20

<210> SEQ ID NO 8
<211> LENGTH: 24
<212> TYPE: PRT
<213> ORGANISM: Sarcophilus harrisii

<400> SEQUENCE: 8

Glu Met Ala Glu His Thr Glu His Leu Lys Ala Asn Asp Asn Leu Lys
1               5                   10                  15

Leu Ser Gln Glu Tyr Glu Ser Ile
            20
```

<210> SEQ ID NO 9
<211> LENGTH: 24
<212> TYPE: PRT
<213> ORGANISM: Mustela putorius

<400> SEQUENCE: 9

```
Asp Met Ala Glu His Thr Glu Arg Leu Lys Ala Asn Asp Ser Leu Lys
1               5                   10                  15

Leu Ser Gln Glu Tyr Glu Ser Ile
            20
```

<210> SEQ ID NO 10
<211> LENGTH: 24
<212> TYPE: PRT
<213> ORGANISM: Galago alleni

<400> SEQUENCE: 10

```
Asp Met Ala Glu His Thr Glu Arg Leu Lys Ala Asn Asp Ser Leu Lys
1               5                   10                  15

Leu Ser Gln Glu Tyr Glu Ser Ile
            20
```

<210> SEQ ID NO 11
<211> LENGTH: 24
<212> TYPE: PRT
<213> ORGANISM: Callithrix aurita

<400> SEQUENCE: 11

```
Asp Met Ala Glu His Thr Glu Arg Leu Lys Ala Asn Asp Ser Leu Lys
1               5                   10                  15

Leu Ser Gln Glu Tyr Glu Ser Ile
            20
```

<210> SEQ ID NO 12
<211> LENGTH: 24
<212> TYPE: PRT
<213> ORGANISM: Rattus rattus

<400> SEQUENCE: 12

```
Asp Met Ala Glu His Thr Glu Arg Leu Lys Ala Asn Asp Ser Leu Lys
1               5                   10                  15

Leu Ser Gln Glu Tyr Glu Ser Ile
            20
```

<210> SEQ ID NO 13
<211> LENGTH: 24
<212> TYPE: PRT
<213> ORGANISM: Mus musculus

<400> SEQUENCE: 13

```
Asp Met Ala Glu His Met Glu Arg Leu Lys Ala Asn Asp Ser Leu Lys
1               5                   10                  15

Leu Ser Gln Glu Tyr Glu Ser Ile
            20
```

<210> SEQ ID NO 14
<211> LENGTH: 24
<212> TYPE: PRT
<213> ORGANISM: Canis familiaris

<400> SEQUENCE: 14

```
Asp Met Ala Glu His Thr Glu Arg Leu Lys Ala Asn Asp Ser Leu Lys
1               5                   10                  15
```

Leu Ser Gln Glu Tyr Glu Ser Ile
            20

<210> SEQ ID NO 15
<211> LENGTH: 24
<212> TYPE: PRT
<213> ORGANISM: Sus barbatus

<400> SEQUENCE: 15

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 16
<211> LENGTH: 24
<212> TYPE: PRT
<213> ORGANISM: Bos primigenius

<400> SEQUENCE: 16

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 17
<211> LENGTH: 24
<212> TYPE: PRT
<213> ORGANISM: Ovis aries

<400> SEQUENCE: 17

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 18
<211> LENGTH: 24
<212> TYPE: PRT
<213> ORGANISM: Orcinus orca

<400> SEQUENCE: 18

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 19
<211> LENGTH: 24
<212> TYPE: PRT
<213> ORGANISM: Saimiri sciureus

<400> SEQUENCE: 19

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 20
<211> LENGTH: 24
<212> TYPE: PRT
<213> ORGANISM: Papio hamadryas

<400> SEQUENCE: 20

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 21
<211> LENGTH: 24
<212> TYPE: PRT
<213> ORGANISM: Primate calicivirus

<400> SEQUENCE: 21

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 22
<211> LENGTH: 24
<212> TYPE: PRT
<213> ORGANISM: Primate calicivirus

<400> SEQUENCE: 22

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 23
<211> LENGTH: 24
<212> TYPE: PRT
<213> ORGANISM: Macaca radiata

<400> SEQUENCE: 23

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 24
<211> LENGTH: 24
<212> TYPE: PRT
<213> ORGANISM: Pan troglodytes

<400> SEQUENCE: 24

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 25
<211> LENGTH: 24
<212> TYPE: PRT
<213> ORGANISM: Homo sapiens

<400> SEQUENCE: 25

Asp Met Ala Glu His Thr Glu Arg Leu Lys Ala Asn Asp Ser Leu Lys
1               5                   10                  15

Leu Ser Gln Glu Tyr Glu Ser Ile
            20

<210> SEQ ID NO 26
<211> LENGTH: 24
<212> TYPE: PRT
<213> ORGANISM: Rattus rattus

<400> SEQUENCE: 26

Asp Leu Ala Asp Asn Ile Glu Arg Leu Lys Ala Asn Asp Gly Leu Lys
1               5                   10                  15

Phe Ser Gln Glu Tyr Glu Ser Ile
            20

<210> SEQ ID NO 27
<211> LENGTH: 24
<212> TYPE: PRT
<213> ORGANISM: Rattus rattus

<400> SEQUENCE: 27

Glu Leu Ala Asp His Ile Glu Arg Leu Lys Ala Asn Asp Asn Leu Lys
1               5                   10                  15

Phe Ser Gln Glu Tyr Glu Ser Ile
            20

<210> SEQ ID NO 28
<211> LENGTH: 24
<212> TYPE: PRT
<213> ORGANISM: Rattus rattus

<400> SEQUENCE: 28

Lys Leu Glu Glu Glu Ile Asn Arg Arg Met Ala Asp Asp Asn Lys Ile
1               5                   10                  15

Phe Arg Glu Glu Phe Asn Ala Leu
            20

<210> SEQ ID NO 29
<211> LENGTH: 10
<212> TYPE: PRT
<213> ORGANISM: Homo sapiens

<400> SEQUENCE: 29

Asp Met Ala Glu His Thr Glu Arg Leu Lys
1               5                   10

<210> SEQ ID NO 30
<211> LENGTH: 4
<212> TYPE: PRT
<213> ORGANISM: Homo sapiens

<400> SEQUENCE: 30

Ala Asn Asp Ser
1

<210> SEQ ID NO 31
<211> LENGTH: 10
<212> TYPE: PRT
<213> ORGANISM: Homo sapiens

<400> SEQUENCE: 31

Leu Lys Leu Ser Gln Glu Tyr Glu Ser Ile
1               5                   10

<210> SEQ ID NO 32
<211> LENGTH: 14
<212> TYPE: PRT

```
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (3)..(3)
<223> OTHER INFORMATION: Xaa is Thr or Met

<400> SEQUENCE: 32

Glu His Xaa Glu Arg Leu Lys Ala Asn Asp Ser Leu Lys Leu
1               5                   10

<210> SEQ ID NO 33
<211> LENGTH: 33
<212> TYPE: PRT
<213> ORGANISM: Xenopus borealis

<400> SEQUENCE: 33

Gly Arg Lys Lys Arg Arg Gln Arg Arg Cys Asp Leu Ala Glu His
1               5                   10                  15

Thr Glu His Leu Lys Ala Asn Asp Asn Leu Lys Ser Gln Glu Tyr Glu
                20                  25                  30

Ser

<210> SEQ ID NO 34
<211> LENGTH: 32
<212> TYPE: PRT
<213> ORGANISM: Anolis carolinensis

<400> SEQUENCE: 34

Gly Arg Lys Lys Arg Arg Gln Arg Arg Cys Asp His Thr Glu His
1               5                   10                  15

Leu Lys Ala Asn Asp Asn Leu Lys Leu Ser Gln Glu Tyr Glu Ser Ile
                20                  25                  30

<210> SEQ ID NO 35
<211> LENGTH: 35
<212> TYPE: PRT
<213> ORGANISM: Danio rerio

<400> SEQUENCE: 35

Gly Arg Lys Lys Arg Arg Gln Arg Arg Cys Glu Leu Ala Glu His
1               5                   10                  15

Thr Glu Leu Leu Lys Ala Asn Asp Asn Leu Lys Leu Ser Gln Glu Tyr
                20                  25                  30

Glu Ser Ile
        35

<210> SEQ ID NO 36
<211> LENGTH: 35
<212> TYPE: PRT
<213> ORGANISM: Tilapia nilotica

<400> SEQUENCE: 36

Gly Arg Lys Lys Arg Arg Gln Arg Arg Cys Glu Leu Ala Glu His
1               5                   10                  15

Thr Glu Leu Leu Lys Ala Asn Asp Asn Leu Lys Leu Ser Gln Glu Tyr
                20                  25                  30

Glu Ser Ile
        35

<210> SEQ ID NO 37
```

```
<211> LENGTH: 35
<212> TYPE: PRT
<213> ORGANISM: Gallus gallus

<400> SEQUENCE: 37

Gly Arg Lys Lys Arg Arg Gln Arg Arg Cys Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 38
<211> LENGTH: 35
<212> TYPE: PRT
<213> ORGANISM: Fringilla coelebs

<400> SEQUENCE: 38

Gly Arg Lys Lys Arg Arg Gln Arg Arg Cys Glu Leu Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 39
<211> LENGTH: 35
<212> TYPE: PRT
<213> ORGANISM: Ornithorhynchus anatinus

<400> SEQUENCE: 39

Gly Arg Lys Lys Arg Arg Gln Arg Arg Cys Glu Leu Ala Glu His
1               5                   10                  15

Thr Asp His Leu Lys Ala Asn Asp Asn Leu Lys Leu Ser Gln Glu Tyr
            20                  25                  30

Glu Ser Ile
        35

<210> SEQ ID NO 40
<211> LENGTH: 35
<212> TYPE: PRT
<213> ORGANISM: Sarcophilus harrisii

<400> SEQUENCE: 40

Gly Arg Lys Lys Arg Arg Gln Arg Arg Cys Glu Met Ala Glu His
1               5                   10                  15

Thr Glu His Leu Lys Ala Asn Asp Asn Leu Lys Leu Ser Gln Glu Tyr
            20                  25                  30

Glu Ser Ile
        35

<210> SEQ ID NO 41
<211> LENGTH: 35
<212> TYPE: PRT
<213> ORGANISM: Mustela putorius

<400> SEQUENCE: 41

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30
```

```
<210> SEQ ID NO 42
<211> LENGTH: 35
<212> TYPE: PRT
<213> ORGANISM: Galago alleni

<400> SEQUENCE: 42

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 43
<211> LENGTH: 35
<212> TYPE: PRT
<213> ORGANISM: Callithrix argentata

<400> SEQUENCE: 43

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 44
<211> LENGTH: 35
<212> TYPE: PRT
<213> ORGANISM: Rattus rattus

<400> SEQUENCE: 44

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 45
<211> LENGTH: 35
<212> TYPE: PRT
<213> ORGANISM: Mus musculus

<400> SEQUENCE: 45

Gly Arg Lys Lys Arg Arg Gln Arg Arg Cys Asp Met Ala Glu His
1               5                   10                  15

Met Glu Arg Leu Lys Ala Asn Asp Ser Leu Lys Leu Ser Gln Glu Tyr
            20                  25                  30

Glu Ser Ile
        35

<210> SEQ ID NO 46
<211> LENGTH: 35
<212> TYPE: PRT
<213> ORGANISM: Canis familiaris

<400> SEQUENCE: 46
```

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 47
<211> LENGTH: 35
<212> TYPE: PRT
<213> ORGANISM: Sus barbatus

<400> SEQUENCE: 47

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 48
<211> LENGTH: 35
<212> TYPE: PRT
<213> ORGANISM: Bos primigenius

<400> SEQUENCE: 48

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 49
<211> LENGTH: 35
<212> TYPE: PRT
<213> ORGANISM: Ovis aries

<400> SEQUENCE: 49

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 50
<211> LENGTH: 35
<212> TYPE: PRT
<213> ORGANISM: Orcinus orca

<400> SEQUENCE: 50

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

```
<210> SEQ ID NO 51
<211> LENGTH: 35
<212> TYPE: PRT
<213> ORGANISM: Saimiri boliviensis

<400> SEQUENCE: 51

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 52
<211> LENGTH: 35
<212> TYPE: PRT
<213> ORGANISM: Papio hamadryas

<400> SEQUENCE: 52

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 53
<211> LENGTH: 35
<212> TYPE: PRT
<213> ORGANISM: Primate calicivirus

<400> SEQUENCE: 53

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 54
<211> LENGTH: 35
<212> TYPE: PRT
<213> ORGANISM: Primate calicivirus

<400> SEQUENCE: 54

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 55
<211> LENGTH: 35
<212> TYPE: PRT
<213> ORGANISM: Macaca arctoides

<400> SEQUENCE: 55

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
```

Glu Ser Ile
        35

<210> SEQ ID NO 56
<211> LENGTH: 35
<212> TYPE: PRT
<213> ORGANISM: Pan troglodytes

<400> SEQUENCE: 56

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 57
<211> LENGTH: 35
<212> TYPE: PRT
<213> ORGANISM: Homo sapiens

<400> SEQUENCE: 57

Gly Arg Lys Lys Arg Arg Gln Arg Arg Cys Asp Met Ala Glu His
1               5                   10                  15

Thr Glu Arg Leu Lys Ala Asn Asp Ser Leu Lys Leu Ser Gln Glu Tyr
            20                  25                  30

Glu Ser Ile
        35

<210> SEQ ID NO 58
<211> LENGTH: 25
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (14)..(14)
<223> OTHER INFORMATION: Xaa is Thr or Met

<400> SEQUENCE: 58

Gly Arg Lys Lys Arg Arg Gln Arg Arg Cys Glu His Xaa Glu Arg
1               5                   10                  15

Leu Lys Ala Asn Asp Ser Leu Lys Leu
            20                  25

<210> SEQ ID NO 59
<211> LENGTH: 18
<212> TYPE: PRT
<213> ORGANISM: Artificial Sequence
<220> FEATURE:
<223> OTHER INFORMATION: Synthetic Construct

<400> SEQUENCE: 59

Thr Ala Thr Asn His Gly Arg Lys Lys Arg Arg Gln Arg Arg Cys
1               5                   10                  15

Asn His

<210> SEQ ID NO 60
<211> LENGTH: 49
<212> TYPE: PRT
<213> ORGANISM: Artificial Sequence

```
<220> FEATURE:
<223> OTHER INFORMATION: Synthetic Construct

<400> SEQUENCE: 60

Pro Arg Arg Ile Ser Pro Asn His Pro Arg Arg Pro Arg Arg Pro Arg
1               5                   10                  15

Arg Pro Arg Arg Pro Arg Arg Asp Met Ala Glu His Met Glu Arg Leu
                20                  25                  30

Lys Ala Asn Asp Ser Leu Lys Leu Ser Gln Glu Tyr Glu Ser Ile Asn
        35                  40                  45

His

<210> SEQ ID NO 61
<211> LENGTH: 29
<212> TYPE: PRT
<213> ORGANISM: Artificial Sequence
<220> FEATURE:
<223> OTHER INFORMATION: Synthetic Construct

<400> SEQUENCE: 61

Asn His Gly Arg Lys Lys Arg Arg Gln Arg Arg Arg Cys Asp Met Ala
1               5                   10                  15

Glu His Met Glu Arg Leu Lys Ala Asn Asp Ser Asn His
                20                  25

<210> SEQ ID NO 62
<211> LENGTH: 29
<212> TYPE: PRT
<213> ORGANISM: Artificial Sequence
<220> FEATURE:
<223> OTHER INFORMATION: Synthetic Construct

<400> SEQUENCE: 62

Asn His Gly Arg Lys Lys Arg Arg Gln Arg Arg Arg Cys Ala Asn Asp
1               5                   10                  15

Ser Leu Lys Leu Ser Gln Glu Tyr Glu Ser Ile Asn His
                20                  25

<210> SEQ ID NO 63
<211> LENGTH: 14
<212> TYPE: PRT
<213> ORGANISM: Artificial Sequence
<220> FEATURE:
<223> OTHER INFORMATION: Synthetic Construct
<220> FEATURE:
<221> NAME/KEY: MISC_FEATURE
<222> LOCATION: (6)..(6)
<223> OTHER INFORMATION: Xaa is Thr or Met

<400> SEQUENCE: 63

Asp Met Ala Glu His Xaa Glu Arg Leu Lys Ala Asn Asp Ser
1               5                   10
```

COMPOSITIONS AND METHODS OF TREATING ROOT AVULSION INJURY

RELATED APPLICATION

This application is a Continuation-in-Part of U.S. patent application Ser. No. 14/391,589, filed Oct. 9, 2014, this application also claims priority from U.S. Provisional Application No. 62/222,578, filed Sep. 23, 2015 and 62/222,663 filed Sep. 23, 2015, the subject matter of which are incorporated herein by reference in their entirety.

GOVERNMENT FUNDING

This invention was made with government support under Grant Nos. NS025713 RES506675 awarded by The National Institutes of Health. The United States government has certain rights to the invention.

TECHNICAL FIELD

This application relates to compositions and methods for treating motor neuron injuries and promoting motor function recovery associated with the motor neuron injuries, and particularly relates to compositions and methods for treating a root avulsion injury and/or denervation induced muscle atrophy.

BACKGROUND

A root avulsion injury physically separates spinal nerves from the spinal cord, leading to severe disruption of the root itself as well as the associated spinal cord segment. Avulsion injuries often occur in violent events, such as traffic and sports accidents or during a difficult childbirth. Following root avulsion, there is severe death of injured neurons, degeneration of axons, scar formation in the spinal cord and loss of synapses, which consequently result in disability of distal muscles and diminution of sensorimotor functions. The avulsed spinal nerve root is made up of a longer distal segment of peripheral nerve and a small fragment of central nervous tissue, which normally forms a dome that protrudes a short distance into the nerve. The interface between the central nervous system (CNS) and peripheral nervous system (PNS) is known as the transitional zone (TZ). The CNS part contains high numbers of astrocytes, which normally form channels within the basal lamina that allow the motor fibers to pass freely into the Schwann cell bands of Bungner. After avulsion injury, remaining astrocytes in the cord rearrange and hypertrophy to form a TZ scar similar to that which is found in a spinal cord injury. In order to restore motor function after avulsion, injured motoneurons must survive and regenerate axons, which need to elongate through inhibitory scar tissue in the TZ before re-entering into the peripheral nerve trunk and eventually form synapses with distal target muscles. Motoneuron survival and axonal regeneration can occur if the roots are surgically reimplanted, using proper techniques, onto the pia mater of the spinal cord close to the vicinity of the damaged ventral motoneuron pools. However, axon regeneration and functional recovery are still quite unsatisfactory. Reactive astrocytes synthesize and secrete inhibitory chondroitin sulfate proteoglycans (CSPGs) into the extracellular matrix, which create a growth impediment. Indeed, CSPGs have been known as the major inhibitor in scar tissue for years and digestion of lesion-induced CSPGs by Chondroitinase ABC (ChABC) enhanced axon regeneration and functional recovery after spinal cord injury.

SUMMARY

Embodiments described herein relate to compositions and methods for treating motor neuron injuries and promoting motor function recovery associated with the motor neuron injuries, and particularly relates to compositions and methods for treating a root avulsion injury and/or denervation induced muscle atrophy.

The methods can include administering to a subject with a motor neuron injury, such as root avulsion injury, and/or denervation induced muscle atrophy a therapeutic agent that inhibits one or more of catalytic activity, signaling, and function of PTPσ.

In some embodiments, the therapeutic agent can include a therapeutic peptide. The therapeutic peptide can have an amino acid sequence that is at least about 65%, at least about 75%, at least about 85%, or at least about 95% homologous to about 10 to about 20 consecutive amino acids of the wedge domain of PTPσ. For example, the therapeutic agent can include a therapeutic peptide that has an amino acid sequence selected from the group consisting of SEQ ID NOs: 1-25, 32, and 63.

In still other embodiments, the therapeutic agent can include a therapeutic peptide that has a sequence identity at least about 65%, at least about 70%, at least about 75%, at least about 80%, at least about 85%, at least about 90%, or at least about 95% homologous to the amino acid sequence of SEQ ID NO: 32. The therapeutic peptide can include, for example, a conservative substitution of an amino acid of at least one, two, three, or four of residue 4, 5, 6, 7, 9, 10, 12, or 13 of SEQ ID NO: 32.

In other embodiments, the therapeutic agent can include a therapeutic peptide that has a sequence identity at least about 65%, at least about 70%, at least about 75%, at least about 80%, at least about 85%, at least about 90%, or at least about 95% homologous to the amino acid sequence of SEQ ID NO: 63. The therapeutic peptide can include, for example, a conservative substitution of an amino acid of at least one, two, three, or four of residue 7, 8, 9, 10, 12, or 13 of SEQ ID NO: 63.

In other embodiments, the therapeutic agent includes a transport moiety that is linked to the therapeutic peptide and facilitates uptake of the therapeutic peptides by a nerve cell, such as a motor neuron. For example, the transport moiety can be an HIV Tat transport moiety or (PRR5) transport moiety.

In still other embodiments, the therapeutic agent can be administered locally to motor nerve cells of the subject or systemically to the subject to treat root avulsion injury and/or denervation induced muscle atrophy.

In some embodiments, the method can further include connecting an avulsed end of a peripheral nerve to a portion of the central nervous system.

The therapeutic agent can be administered at an amount effective to increase survival rate of injured motoneurons, enhance regrowth across inhibitory central nervous system scar into re-implanted spinal roots, regenerate axons, decrease muscle atrophy, and/or promote motor functional recovery.

BRIEF DESCRIPTION OF THE DRAWINGS

FIGS. 7A-C illustrate: (A-B) Images showing the wedge domain of PTPσ is truncated into two separate peptides, each containing an alpha helix and the turn region. These truncations were synthesized as peptides with a terminus TAT domain and C terminus amidation (SEQ ID NOs: 61 and 62). In addition, a separate cytosolic penetration domain is utilized instead of Tat (PRR5) (SEQ ID NO: 60). (C) A graph shows the total number of crossings per gradient is divided by the number of neuronal bodies within each gradient. The total is normalized to 2.5 µM ISP in each experiment and represented as averages. While Tat itself is not effective over vehicle control, both PRR5-ISP and Truncation 1 are capable of replicating the ISP effect. This suggests that only the first alpha helix is necessary for ISP function within the cell. Error Bar=SEM.

DETAILED DESCRIPTION

Figure 1:
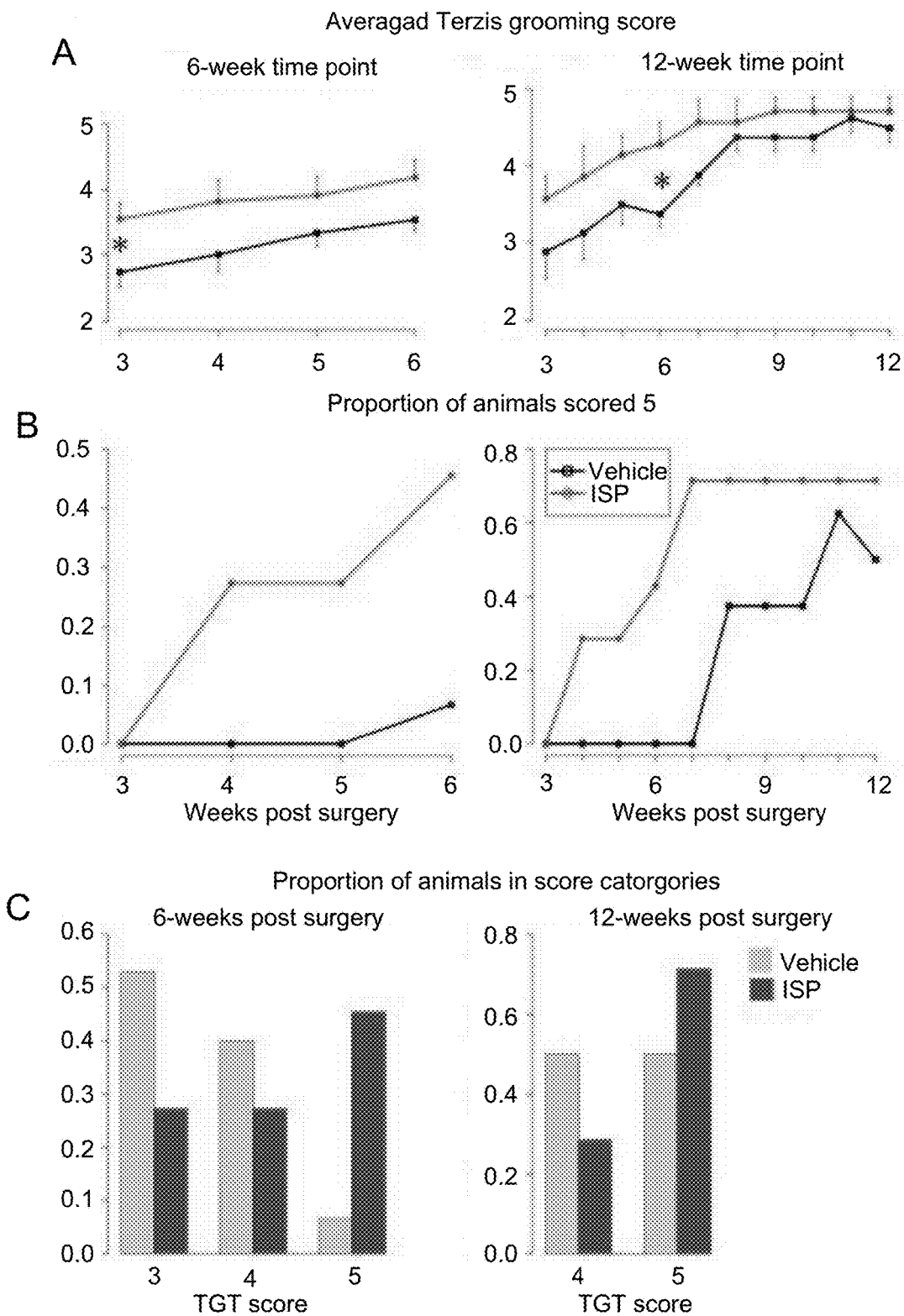
FIGS. 1A-C illustrate plots and graphs showing ISP treatment enhanced motor functional recovery after root avulsion injury/re-implantation repair, reflected by the Terzis grooming test. All left panels were abstracted from 6-week time point (n=15 for vehicle, n=11 for ISP), while right panel from 12-week time point (n=8 for vehicle, n=7 for ISP). (A) Averaged Terzis grooming test score was increased by ISP treatment. Data is expressed as mean+s.e.m for ISP group, or as mean−s.e.m for vehicle group. (* p<0.05, Mann-Whitney U test). (B) Animals scored 5, indicating complete grooming recovery, accounted for higher percentage in ISP groups than vehicles. (C) Proportion of animals in each TGT score category at 6- and 12-week postoperatively. Vehicle rats had higher tendency to have a 3 or 4 score but less frequency to score 5.

The embodiments described herein are not limited to the particular methodology, protocols, and reagents, etc., and as such may vary. The terminology used herein is for the purpose of describing particular embodiments only, and is not intended to limit the scope of the present invention, which is defined solely by the claims. Other than in the operating examples, or where otherwise indicated, all numbers expressing quantities of ingredients or reaction conditions used herein should be understood as modified in all instances by the term "about."

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

Unless otherwise defined, scientific and technical terms used herein shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well known and commonly used in the art.

As used herein, "one or more of a, b, and c" means a, b, c, ab, ac, bc, or abc. The use of "or" herein is the inclusive or.

The term "administering" to a patient includes dispensing, delivering or applying an active compound in a pharmaceutical formulation to a subject by any suitable route for delivery of the active compound to the desired location in the subject (e.g., to thereby contact a desired cell such as a desired neuron), including administration into the cerebrospinal fluid or across the blood-brain barrier, delivery by either the parenteral or oral route, intramuscular injection, subcutaneous or intradermal injection, intravenous injection, buccal administration, transdermal delivery and administration by the rectal, colonic, vaginal, intranasal or respiratory tract route. The agents may, for example, be administered to a comatose, anesthetized or paralyzed subject via an intravenous injection or may be administered intravenously to a pregnant subject to stimulate axonal growth in a fetus. Specific routes of administration may include topical application (such as by eyedrops, creams or erodible formulations to be placed under the eyelid, intraocular injection into the aqueous or the vitreous humor, injection into the external layers of the eye, such as via subconjunctival injection or subtenon injection, parenteral administration or via oral routes.

The term "antibody", includes human and animal mAbs, and preparations of polyclonal antibodies, synthetic antibodies, including recombinant antibodies (antisera), chimeric antibodies, including humanized antibodies, anti-idiotopic antibodies and derivatives thereof. A portion or fragment of an antibody refers to a region of an antibody that retains at least part of its ability (binding specificity and affinity) to bind to a specified epitope. The term "epitope" or "antigenic determinant" refers to a site on an antigen to which antibody paratope binds. Epitopes formed from contiguous amino acids are typically retained on exposure to denaturing solvents whereas epitopes formed by tertiary folding are typically lost on treatment with denaturing solvents. An epitope typically includes at least 3, at least 5, or 8 to 10, or about 13 to 15 amino acids in a unique spatial conformation. Methods of determining spatial conformation of epitopes include, for example, x-ray crystallography and 2-dimensional nuclear magnetic resonance.

The terms axonal "growth" or "outgrowth" (also referred to herein as "neuronal outgrowth") includes the process by which axons or dendrites extend from a neuron. The outgrowth can result in a new neuritic projection or in the extension of a previously existing cellular process. "Stimulating axonal growth" means promoting axonal outgrowth.

The term "dieback" refers to axonal retraction that occurs as a result of trauma to the axon.

The terms "chimeric protein" or "fusion protein" refer to a fusion of a first amino acid sequence encoding a polypeptide with a second amino acid sequence defining a domain (e.g., polypeptide portion) foreign to and not substantially homologous with the domain of the first polypeptide. A chimeric protein may present a foreign domain, which is found (albeit in a different protein) in an organism, which also expresses the first protein, or it may be an "interspecies", "intergenic", etc. fusion of protein structures expressed by different kinds of organisms.

The term "contacting neurons" or "treating neurons" refers to any mode of agent delivery or "administration," either to cells or to whole organisms, in which the agent is capable of exhibiting its pharmacological effect in neurons. "Contacting neurons" includes both in vivo and in vitro methods of bringing an agent of the invention into proximity with a neuron. Suitable modes of administration can be determined by those skilled in the art and such modes of administration may vary between agents. For example, when axonal growth of neurons is stimulated ex vivo, agents can be administered, for example, by transfection, lipofection, electroporation, viral vector infection, or by addition to growth medium.

An "effective amount" of an agent or therapeutic peptide is an amount sufficient to achieve a desired therapeutic or pharmacological effect, such as an amount that is capable of activating the growth of neurons. An effective amount of an agent as defined herein may vary according to factors such as the disease state, age, and weight of the subject, and the ability of the agent to elicit a desired response in the subject. Dosage regimens may be adjusted to provide the optimum therapeutic response. An effective amount is also one in which any toxic or detrimental effects of the active compound are outweighed by the therapeutically beneficial effects.

The term "expression" refers to the process by which nucleic acid is translated into peptides or is transcribed into RNA, which, for example, can be translated into peptides, polypeptides or proteins. If the nucleic acid is derived from genomic DNA, expression may, if an appropriate eukaryotic host cell or organism is selected, include splicing of the mRNA. For heterologous nucleic acid to be expressed in a host cell, it must initially be delivered into the cell and then, once in the cell, ultimately reside in the nucleus.

The term "genetic therapy" involves the transfer of heterologous DNA to cells of a mammal, particularly a human, with a disorder or conditions for which therapy or diagnosis is sought. The DNA is introduced into the selected target cells in a manner such that the heterologous DNA is expressed and a therapeutic product encoded thereby is produced. Alternatively, the heterologous DNA may in some manner mediate expression of DNA that encodes the therapeutic product; it may encode a product, such as a peptide or RNA that in some manner mediates, directly or indirectly, expression of a therapeutic product. Genetic therapy may also be used to deliver nucleic acid encoding a gene product to replace a defective gene or supplement a gene product produced by the mammal or the cell in which it is introduced. The heterologous DNA encoding the therapeutic product may be modified prior to introduction into the cells of the afflicted host in order to enhance or otherwise alter the product or expression thereof.

The term "gene" or "recombinant gene" refers to a nucleic acid comprising an open reading frame encoding a polypeptide, including both exon and (optionally) intron sequences.

The term "heterologous nucleic acid sequence" is typically DNA that encodes RNA and proteins that are not normally produced in vivo by the cell in which it is expressed or that mediates or encodes mediators that alter expression of endogenous DNA by affecting transcription, translation, or other regulatable biochemical processes. A heterologous nucleic acid sequence may also be referred to as foreign DNA. Any DNA that one of skill in the art would recognize or consider as heterologous or foreign to the cell in which it is expressed is herein encompassed by heterologous DNA. Examples of heterologous DNA include, but are not limited to, DNA that encodes traceable marker proteins, such as a protein that confers drug resistance, DNA that encodes therapeutically effective substances, such as anticancer agents, enzymes and hormones, and DNA that encodes other types of proteins, such as antibodies. Antibodies that are encoded by heterologous DNA may be secreted or expressed on the surface of the cell in which the heterologous DNA has been introduced.

The terms "homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

The term "neuronal migration" refers to the ability of neuronal cells to migrate or neuronal processes to migrate, such as an axonal or dendritic migration.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into a target tissue, such that it enters the animal's system and, thus, is subject to metabolism and other like processes, for example, subcutaneous administration.

The term "patient" or "subject" or "animal" or "host" refers to any mammal. The subject may be a human, but can also be a mammal in need of veterinary treatment, e.g., domestic animals (e.g., dogs, cats, and the like), farm animals (e.g., cows, sheep, fowl, pigs, horses, and the like) and laboratory animals (e.g., rats, mice, guinea pigs, and the like).

The term "peripheral nervous system (PNS) neurons" includes the neurons which reside or extend outside of the CNS. PNS is intended to include the neurons commonly understood as categorized in the peripheral nervous system, including sensory neurons and motor neurons.

The terms "polynucleotide sequence" and "nucleotide sequence" are also used interchangeably herein.

The terms "peptide" or "polypeptide" are used interchangeably herein and refer to compounds consisting of from about 2 to about 90 amino acid residues, inclusive, wherein the amino group of one amino acid is linked to the carboxyl group of another amino acid by a peptide bond. A peptide can be, for example, derived or removed from a native protein by enzymatic or chemical cleavage, or can be prepared using conventional peptide synthesis techniques (e.g., solid phase synthesis) or molecular biology techniques (see Sambrook et al., MOLECULAR CLONING: LAB. MANUAL (Cold Spring Harbor Press, Cold Spring Harbor, N.Y., 1989)). A "peptide" can comprise any suitable L- and/or D-amino acid, for example, common a-amino acids (e.g., alanine, glycine, valine), non-a-amino acids (e.g., P-alanine, 4-aminobutyric acid, 6aminocaproic acid, sarcosine, statine), and unusual amino acids (e.g., citrulline, homocitruline, homoserine, norleucine, norvaline, ornithine) The amino, carboxyl and/or other functional groups on a peptide can be free (e.g., unmodified) or protected with a suitable protecting group. Suitable protecting groups for amino and carboxyl groups, and means for adding or removing protecting groups are known in the art. See, e.g., Green & Wuts, PROTECTING GROUPS IN ORGANIC SYNTHESIS (John Wiley & Sons, 1991). The functional groups of a peptide can also be derivatized (e.g., alkylated) using art-known methods.

Peptides can be synthesized and assembled into libraries comprising a few too many discrete molecular species. Such libraries can be prepared using well-known methods of combinatorial chemistry, and can be screened as described herein or using other suitable methods to determine if the library comprises peptides which can antagonize CSPG-PTPσ interaction. Such peptide antagonists can then be isolated by suitable means.

The term "peptidomimetic", refers to a protein-like molecule designed to mimic a peptide. Peptidomimetics typically arise either from modification of an existing peptide, or by designing similar systems that mimic peptides, such as peptoids and β-peptides. Irrespective of the approach, the altered chemical structure is designed to advantageously adjust the molecular properties such as, stability or biological activity. These modifications involve changes to the peptide that do not occur naturally (such as altered backbones and the incorporation of nonnatural amino acids).

The terms "prevent" or "preventing" refer to reducing the frequency or severity of a disease or condition. The term does not require an absolute preclusion of the disease or condition. Rather, this term includes decreasing the chance for disease occurrence. For example, disclosed are methods of reducing the occurrence and/or severity of a root avulsion injury in a subject, comprising administering to the root avulsion injury of the subject a therapeutically effective amount of a composition comprising a therapeutic agent.

The term "retraction" refers to the receding of the axon away from the site of injury, such as from where the glial scar forms. Here, the end of regenerating axons stop extending and become dystrophic. These dystrophic ends then can recede further from the glial scar and the site of injury.

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

The term "recombinant," as used herein, means that a protein is derived from a prokaryotic or eukaryotic expression system.

The term "therapeutically effective" means that the amount of the composition used is of sufficient quantity to ameliorate one or more causes, symptoms, or sequelae of a disease or disorder. Such amelioration only requires a reduction or alteration, not necessarily elimination, of the causes, symptoms, or sequelae of a disease or disorder.

The term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well. The term "transfection" is used to refer to the uptake of foreign DNA by a cell. A cell has been "transfected" when exogenous DNA has been introduced inside the cell membrane. A number of transfection techniques are generally known in the art. See, e.g., Graham et al., Virology 52:456 (1973); Sambrook et al., Molecular Cloning: A Laboratory Manual (1989); Davis et al., Basic Methods in Molecular Biology (1986); Chu et al., Gene 13:197 (1981). Such techniques can be used to introduce one or more exogenous DNA moieties, such as a nucleotide integration vector and other nucleic acid molecules, into suitable host cells. The term captures chemical, electrical, and viral-mediated transfection procedures.

The terms "transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence), which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

The term "sympathetic nervous system" refers to the thoracolumbar division of the autonomic nervous system, which is responsible for helping to regulate a variety of body functions, including heart rate, breathing, sweating, and digestion.

The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder.

The term "vector" refers to a nucleic acid molecule capable of transporting another nucleic acid to which it has been linked. Preferred vectors are those capable of one or more of, autonomous replication and expression of nucleic acids to which they are linked. Vectors capable of directing the expression of genes to which they are operatively linked are referred to herein as "expression vectors".

The term "wild type" refers to the naturally-occurring polynucleotide sequence encoding a protein, or a portion thereof, or protein sequence, or portion thereof, respectively, as it normally exists in vivo. As used herein, the term "nucleic acid" refers to polynucleotides, such as deoxyribonucleic acid (DNA), and, where appropriate, ribonucleic acid (RNA). The term should also be understood to include, as equivalents, analogs of either RNA or DNA made from nucleotide analogs, and, as applicable to the embodiment being described, single (sense or antisense) and double-stranded polynucleotides.

The agents, compounds, compositions, antibodies, etc. used in the methods described herein are considered to be purified and/or isolated prior to their use. Purified materials are typically "substantially pure", meaning that a nucleic acid, polypeptide or fragment thereof, or other molecule has been separated from the components that naturally accompany it. Typically, the polypeptide is substantially pure when it is at least 60%, 70%, 80%, 90%, 95%, or even 99%, by weight, free from the proteins and other organic molecules with which it is associated naturally. For example, a substantially pure polypeptide may be obtained by extraction from a natural source, by expression of a recombinant nucleic acid in a cell that does not normally express that protein, or by chemical synthesis. "Isolated materials" have been removed from their natural location and environment. In the case of an isolated or purified domain or protein fragment, the domain or fragment is substantially free from amino acid sequences that flank the protein in the naturally-occurring sequence. The term "isolated DNA" means DNA has been substantially freed of the genes that flank the given DNA in the naturally occurring genome. Thus, the term "isolated DNA" encompasses, for example, cDNA, cloned genomic DNA, and synthetic DNA.

The terms "portion", "fragment", "variant", "derivative" and "analog", when referring to a polypeptide include any polypeptide that retains at least some biological activity referred to herein (e.g., inhibition of an interaction such as binding). Polypeptides as described herein may include portion, fragment, variant, or derivative molecules without limitation, as long as the polypeptide still serves its function. Polypeptides or portions thereof of the present invention may include proteolytic fragments, deletion fragments and in particular, or fragments that more easily reach the site of action when delivered to an animal.

Embodiments described herein relate to compositions and methods for treating motor neuron injuries and promoting motor function recovery associated with the motor neuron injuries, and particularly relates to compositions and methods for treating a root avulsion injury and/or denervation induced muscle atrophy.

When a root avulsion injury occurs, the rupture site tends to localize in the CNS-PNS transitional zone. Thus, spinal root avulsion injury is unusual in that it affects both PNS and CNS tissues simultaneously. In addition, a large proportion of affected motoneurons eventually die. This is likely due to the close proximity of the lesion to the cell body. Also, the suboptimal ability of axons to bypass the transitional zone coupled with the long distances and limited elongation speed due to CSPG accumulation along the length of the re-implanted nerve proper, together lead to prolonged and inefficient regeneration. All of these factors contribute to atrophy of distal muscle and loss of motor functions after avulsion injury even with re-implantation.

In responds to root avulsion injury, abundant astrocytes in the CNS-PNS transitional zone are activated and synthesize CSPGs in hours, depositing them in extracellular matrices of the scar. The deposited CGPGs can act as an impediment to nerve growth and axonal extension. We found that local systemic blocking of PTPσ signaling or function after spinal root avulsion injury can remarkably promote nerve regeneration, resulting in 1) increased survival rate of injured motoneurons; 2) enhanced regrowth across inhibitory CNS scar into the re-implanted spinal roots; 3) more regenerated axons with enlarged size in peripheral nerve trunk; 4) decreased muscle atrophy; and 5) more rapid motor functional recovery accompanied by reductions in electromyography abnormalities.

Accordingly, in some embodiments described herein a therapeutic agent that inhibits one or more of catalytic activity, signaling, and function of PTPσ can be administered to a subject with a motor neuron injury, such as root avulsion injury, and/or denervation induced muscle atrophy to enhance axon outgrowth and or enhance functional return.

The activity, signaling, and/or function of PTPσ can be suppressed, inhibited, and/or blocked in several ways including: direct inhibition of the activity of the intracellular domain of the PTPσ (e.g., by using small molecules, peptidomimetics, antibodies, intrabodies, or dominant negative polypeptides); activation of genes and/or proteins that inhibit one or more of, the activity, signaling, and/or function of the intracellular domain of PTPσ (e.g., by increasing the expression or activity of the genes and/or proteins); inhibition of genes and/or proteins that are downstream mediators of the PTPσ (e.g., by blocking the expression and/or activity of the mediator genes and/or proteins); introduction of genes and/or proteins that negatively regulate one or more of, activity, signaling, and/or function of PTPσ (e.g., by using recombinant gene expression vectors, recombinant viral vectors or recombinant polypeptides); or gene replacement with, for instance, a hypomorphic mutant of PTPσ (e.g., by homologous recombination, overexpression using recombinant gene expression or viral vectors, or mutagenesis).

The therapeutic agent that inhibits or reduces one or more of the activity, signaling, and/or function of PTPσ can include an agent that decreases and/or suppresses the activity, signaling, and/or function of PTPσ without inhibiting binding to or activation the LAR family phosphatases by proteoglycans, such as CSPG. Such agents can be delivered intracellularly and once delivered intracellularly promote the intrinsic growth capability of a nerve cell, such as a motor nerve cell, activate the growth pathway of neurons and are capable of producing a neurosalutary effect.

The neurosalutary effect can include a response or result favorable to the health or function of a neuron, of a part of the nervous system, or of the nervous system generally. Examples of such effects include improvements in the ability of a neuron or portion of the nervous system to resist insult, to regenerate, to maintain desirable function, to grow or to survive. The neurosalutary effect can include producing or effecting such a response or improvement in function or resilience within a component of the nervous system. Examples of producing a neurosalutary effect would include stimulating axonal outgrowth after injury to a neuron; rendering a neuron resistant to apoptosis; rendering a neuron resistant to a toxic compound; reversing age-related neuronal atrophy or loss of function; reversing and/or reducing dieback, and/or promoting neural sprouting.

In some embodiments, the therapeutic agent that inhibits or reduces one or more of the activity, signaling, and/or function of PTPσ, can include a therapeutic peptide or small molecule that binds to and/or complexes with the intracellular domain of PTPσ, in particular, the intracellular wedge shaped domain, to inhibit the activity, signaling, and/or function of PTPσ. Accordingly, therapeutic peptides or small molecules that bind to and/or complex with the intracellular domain of PTPσ of neural cells can be used to promote cell growth, motility, survival and plasticity of these cells.

The therapeutic agent can be a peptide mimetic of the wedge shaped domain (i.e., wedge domain) of the intracellular catalytic domain of PTPσ, such as described, for example, in WO 2013/155103A1, which is herein incorporated by reference in its entirety. Peptide mimetics of the wedge domain of the PTPσ when expressed in cells (e.g., neural cells) or conjugated to an intracellular transport moiety can bind to the wedge domain and be used to abolish PTPσ signaling in a neural cell activated with CSPGs to promote cell growth, motility, and survival. Binding of these therapeutic peptides to PTPσ intact wedge domain can potentially: (i) interfere with the ability for PTPσ to interact with target proteins, such as phosphatase targets; (ii) interfere with activity promoting intermolecular interactions between PTPσ and another domain contained in PTPσ, such as the catalytically inactive second phosphatase domain D2; (iii) prevent access of proteins to the active phosphatase site; (iv) out-compete normal interactors of the wedge domain; and/or (v) sterically inhibit phosphatase activity.

In some embodiments, the peptide mimetic (i.e., therapeutic peptide) can include, consist essentially, and/or consist of about 10 to about 20 amino acids and have an amino acid sequence that is at least about 65%, at least about 70%, at least about 75%, at least about 80%, at least about 85%, at least about 90%, at least about 95%, or about 100% homologous or identical to an about 10 to about 20 consecutive amino acid portion of the amino acid sequence of the wedge domain of PTPσ. In some embodiments, the about 10 to about 20 consecutive amino acid portion includes consecutive amino acids of N-terminal alpha helix and 4 amino acid turn of the wedge domain.

A peptide (e.g., therapeutic peptide) corresponding to or substantially homologous to the wedge domain of PTPσ with a cytosolic-carrier was able to relieve CSPG-mediated inhibition, allowing neurons to advance on CSPG substrates instead of typical inhibition. This effect was dose dependent and reliant on the responding cell expressing PTPσ. This peptide can be given locally to a tissue of interest or in need thereof of a subject or systemically to a subject in need thereof to promote plasticity and functional recovery following root avulsion injury.

As shown in Table 1, the wedge domain sequence of PTPσ is highly conserved among higher mammals, with only a single amino acid change in mouse and rats (Threonine to Methithione at position 6) preventing 100% homology.

TABLE 2

Wedge Domain Alignment

| 01 | 2 | 3 | 4 | 5 | 6 | 7 | 8 | 9 | 10 | 1 | 2 | 3 | 4 | 5 | 6 | 7 | 8 | 9 | 20 | 1 | 2 | 3 | 4 | Species | SEQ ID |
|---|---|---|---|---|---|---|---|---|---|---|---|---|---|---|---|---|---|---|---|---|---|---|---|---|---|
| D | L | A | E | H | T | E | H | L | K | A | N | D | N | L | K | | S | Q | E | Y | E | S | | Xenopus | SEQ ID NO: 1 |
| D | H | T | E | H | | | | L | K | A | N | D | N | L | K | L | S | Q | E | Y | E | S | I | Green anole | SEQ ID NO: 2 |
| E | L | A | E | H | T | E | L | L | K | A | N | D | N | L | K | L | S | Q | E | Y | E | S | I | Zebrafish | SEQ ID NO: 3 |
| E | L | A | E | H | T | E | L | L | K | A | N | D | N | L | K | L | S | Q | E | Y | E | S | I | Talapia | SEQ ID NO: 4 |
| E | L | A | E | H | T | E | H | L | K | A | N | D | N | L | K | L | S | Q | E | Y | E | S | I | Chicken | SEQ ID NO: 5 |
| E | L | A | E | H | T | E | H | L | K | A | N | D | N | L | K | L | S | Q | E | Y | E | S | I | Finch | SEQ ID NO: 6 |
| E | L | A | E | H | T | D | H | L | K | A | N | D | N | L | K | L | S | Q | E | Y | E | S | I | Platypus | SEQ ID NO: 7 |
| E | M | A | E | H | T | E | H | L | K | A | N | D | N | L | K | L | S | Q | E | Y | E | S | I | Tazmanian Devil | SEQ ID NO: 8 |
| D | M | A | E | H | T | E | R | L | K | A | N | D | S | L | K | L | S | Q | E | Y | E | S | I | Ferret | SEQ ID NO: 9 |
| D | M | A | E | H | T | E | R | L | K | A | N | D | S | L | K | L | S | Q | E | Y | E | S | I | Bush-Baby | SEQ ID NO: 10 |
| D | M | A | E | H | T | E | R | L | K | A | N | D | S | L | K | L | S | Q | E | Y | E | S | I | Marmoset | SEQ ID NO: 11 |
| D | M | A | E | H | T | E | R | L | K | A | N | D | S | L | K | L | S | Q | E | Y | E | S | I | RAT | SEQ ID NO: 12 |
| D | M | A | E | H | M | E | R | L | K | A | N | D | S | L | K | L | S | Q | E | Y | E | S | I | Mouse | SEQ ID NO: 13 |
| D | M | A | E | H | T | E | R | L | K | A | N | D | S | L | K | L | S | Q | E | Y | E | S | I | Dog | SEQ ID NO: 14 |
| D | M | A | E | H | T | E | R | L | K | A | N | D | S | L | K | L | S | Q | E | Y | E | S | I | Pig | SEQ ID NO: 15 |
| D | M | A | E | H | T | E | R | L | K | A | N | D | S | L | K | L | S | Q | E | Y | E | S | I | Cow | SEQ ID NO: 16 |
| D | M | A | E | H | T | E | R | L | K | A | N | D | S | L | K | L | S | Q | E | Y | E | S | I | Sheep | SEQ ID NO: 17 |
| D | M | A | E | H | T | E | R | L | K | A | N | D | S | L | K | L | S | Q | E | Y | E | S | I | Killer Whale | SEQ ID NO: 18 |
| D | M | A | E | H | T | E | R | L | K | A | N | D | S | L | K | L | S | Q | E | Y | E | S | I | Squirrel Monkey | SEQ ID NO: 19 |
| D | M | A | E | H | T | E | R | L | K | A | N | D | S | L | K | L | S | Q | E | Y | E | S | I | Baboon | SEQ ID NO: 20 |
| D | M | A | E | H | T | E | R | L | K | A | N | D | S | L | K | L | S | Q | E | Y | E | S | I | Gorilla | SEQ ID NO: 21 |
| D | M | A | E | H | T | E | R | L | K | A | N | D | S | L | K | L | S | Q | E | Y | E | S | I | Gibbon | SEQ ID NO: 22 |
| D | M | A | E | H | T | E | R | L | K | A | N | D | S | L | K | L | S | Q | E | Y | E | S | I | Macaque | SEQ ID NO: 23 |
| D | M | A | E | H | T | E | R | L | K | A | N | D | S | L | K | L | S | Q | E | Y | E | S | I | Chimpanzee | SEQ ID NO: 24 |
| D | M | A | E | H | T | E | R | L | K | A | N | D | S | L | K | L | S | Q | E | Y | E | S | I | Human | SEQ ID NO: 25 |
| D | L | A | D | N | I | E | R | L | K | A | N | D | G | L | K | F | S | Q | E | Y | E | S | I | LAR (Lar family) | SEQ ID NO: 26 |
| E | L | A | D | H | I | E | R | L | K | A | N | D | N | L | K | F | S | Q | E | Y | E | S | I | Delta (Lar family) | SEQ ID NO: 27 |
| K | L | E | E | E | I | N | R | R | M | A | D | D | N | K | I | F | R | E | E | F | N | A | L | ptp alpha | SEQ ID NO: 28 |

As shown in Table 1, the first alpha helix of the wedge domain of PTPσ includes amino acids 1-10, the turn region includes amino acids 11-14, and the second alpha helix includes amino acids 15-24. For example, the first alpha helix of the wedge domain of human PTPσ has the amino acid sequence of DMAEHTERLK (SEQ ID NO: 29), the turn has the amino acid sequence of ANDS (SEQ ID NO: 30), and the second alpha helix has the amino acid sequence of LKLSQEYESI (SEQ ID NO: 31).

The wedge domain also shares sequence homology with the other members of the LAR family, LAR and PTPdelta. It is likely that these amino acids are necessary for the overall structure of the wedge domain. Conserved amino acids include an alanine at position 13, which marks the end of the first alpha helix and the start of the turn, making it likely to be necessary for general wedge size and structure.

Since the general secondary and tertiary structures of the wedge domain remain consistent through most receptor PTPs, several conservative substitutions can be made to a therapeutic peptide targeting the PTPσ wedge domain to obtain similar results. Examples of conservative substitutions include the substitution of one non-polar (hydrophobic) residue, such as isoleucine, valine, leucine or methionine for another, the substitution of one polar (hydrophilic) residue for another, such as between arginine and lysine, between glutamine and asparagine, between glycine and serine, the substitution of one basic residue such as lysine, arginine or histidine for another, and/or the substitution of one acidic residue, such as aspartic acid or glutamic acid for another.

These conservative substitutions can occur in the non-unique domains in either alpha helix or the turn, specifically positions 1-3 and 7-10 in the first alpha helix; 12 and 13 in the turn; and 15, 16, 18-24 in the second alpha helix. These amino acids may be necessary to the overall structure of the wedge domain, but not necessary for specificity of binding of wedge to PTPσ.

The unique amino acids to PTPσ, particularly the amino acids expressed differentially in PTPσ vs LAR, were found to be necessary for specificity of wedge domain binding. These include an EH domain in the first alpha helix position 4 and 5 followed by a threonine or a metathione (rat and mouse substitution) at position 6. In the turn, there is a unique serine at position 14 in all higher mammals. Finally, there is a unique leucine at position 17 in the second alpha helix. The potential roles of these unique amino acids will be discussed below.

The serine residue in the turn at position 14 is of particular interest due to its location in the wedge domain. This amino acid, located in the turn between alpha helixes, is slightly extended from the general secondary and tertiary structure of PTPσ, making it available for binding interactions. In addition, serine, due to its hydroxyl group and the polarity it contains, is known to facilitate several homophillic and heterophillic binding events, such as hydrogen binding between adjacent serines. Serines are also known to undergo various modifications, such as phosphorylation, making the likelihood of its necessity for specificity high. It is possible that smaller peptides that focus on the turn in the wedge domain and include the conserved serine may offer greater stability with similar function. Such peptides can be synthesized as loops, with cysteine's on either end to created di-sulfide bonds.

The unique amino acids in the first alpha helix include glutamic acid at position 4, histidine at position 5 and threonine or metathione at position 6. Although the histidine is implicated in the consensus wedge domain, it is not found in LAR, PTPdelta, PTPmu or CD45. As all three of these amino acids are either charged or polar, it is likely that either this sequence or one of its components is necessary for PTPσ wedge specificity.

Additionally, the second alpha helix contains a unique leucine at position 17. Leucines have been implicated as the critical adhesive molecules for the three dimensional structure of leucine zippers. In these molecules, which are structurally similar to wedge domains, leucines of opposing alpha helixes, located at approximately 7 intervals, interact with hydrophobic regions of the opposing alpha helix. As there is also a Leucine in the first alpha helix, located at position 9, it is believed that this unique leucine is necessary for the overall three-dimensional structural integrity of the PTPσ wedge.

Accordingly, in other embodiments, the therapeutic peptide can include, consist essentially of, or consist of about 14 to about 20 amino acids and include the amino acid sequence EH$X_1$ERLKANDSLKL (SEQ ID NO: 32), wherein $X_1$ is T or M. A therapeutic peptide including SEQ ID NO: 32 can include at least one, at least two, at least three, at least four, or at least five conservative substitutions so that the therapeutic peptide has an amino acid sequence that is at least about 65%, at least about 70%, at least about 75%, at least about 80%, at least about 85%, at least about 90%, or at least about 95% homologous to SEQ ID NO: 32.

In some embodiments, the conservative substitutions can be of amino acid residues 4E, 5R, 6L, 7K, 9N, 10D, 12L, or 13K of SEQ ID NO: 32. By way of example, amino acid residue 4E can be substituted with D or Q, amino acid residue 5R can be substituted with H, L, or K, amino acid residue 6L can be substituted with I, V, or M, amino acid residue 7K can be substituted with R or H, amino acid residue 9N can be substituted with E or D, amino acid residue 10 D can be substituted with E or N, amino acid residue 12L can be substituted with I, V, or M, and/or amino acid residue 13K can be substituted with R or H.

In other embodiments, the therapeutic peptide can include, consist essentially of, or consist of about 14 to about 20 amino acids and include the amino acid sequence DMAEH$X_1$ERLKANDS (SEQ ID NO: 63), wherein $X_1$ is T or M. A therapeutic peptide including SEQ ID NO: 63 can include at least one, at least two, at least three, at least four, or at least five conservative substitutions so that the therapeutic peptide has an amino acid sequence that is at least about 65%, at least about 70%, at least about 75%, at least about 80%, at least about 85%, at least about 90%, or at least about 95% homologous to SEQ ID NO: 63.

In some embodiments, the conservative substitutions can be of amino acid residues 7E, 8R, 9L, 10K, 12N, or 13D of SEQ ID NO: 63. By way of example, amino acid residue 7E can be substituted with D or Q, amino acid residue 8R can be substituted with H, L, or K, amino acid residue 9L can be substituted with I, V, or M, amino acid residue 10K can be substituted with R or H, amino acid residue 12N can be substituted with E or D, and amino acid residue 13 D can be substituted with E or N.

The therapeutic peptides described herein can be subject to other various changes, substitutions, insertions, and deletions where such changes provide for certain advantages in its use. In this regard, therapeutic peptides that bind to and/or complex with a wedge domain of PTPσ can correspond to or be substantially homologous with, rather than be identical to, the sequence of a recited polypeptide where one or more changes are made and it retains the ability to inhibits or reduces one or more of the activity, signaling, and/or function of PTPσ function.

The therapeutic polypeptide can be in any of a variety of forms of polypeptide derivatives that include amides, conjugates with proteins, cyclized polypeptides, polymerized polypeptides, analogs, fragments, chemically modified polypeptides and the like derivatives.

It will be appreciated that the conservative substitution can also include the use of a chemically derivatized residue in place of a non-derivatized residue provided that such peptide displays the requisite binding activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-im-benzylhistidine. Also included as chemical derivatives are those polypeptides, which contain one or more naturally occurring amino acid derivatives of the twenty standard amino acids. For example: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides described herein may also include any polypeptide having one or more additions and/or deletions or residues relative to the sequence of a polypeptide whose sequence is shown herein, so long as the requisite activity is maintained.

One or more of peptides of the therapeutic peptides described herein can also be modified by natural processes, such as posttranslational processing, and/or by chemical modification techniques, which are known in the art. Modifications may occur in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Peptides and/or proteins described herein may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may function as inhibitors of the LAR family phosphatases (without being restricted to the present examples).

The therapeutic polypeptides described herein may be prepared by methods known to those skilled in the art. The peptides and/or proteins may be prepared using recombinant DNA. For example, one preparation can include cultivating a host cell (bacterial or eukaryotic) under conditions, which provide for the expression of peptides and/or proteins within the cell.

The purification of the polypeptides may be done by affinity methods, ion exchange chromatography, size exclusion chromatography, hydrophobicity or other purification technique typically used for protein purification. The purification step can be performed under non-denaturing conditions. On the other hand, if a denaturing step is required, the protein may be renatured using techniques known in the art.

In some embodiments, the therapeutic peptides described herein can include additional residues that may be added at either terminus of a polypeptide for the purpose of providing a "linker" by which the polypeptides can be conveniently linked and/or affixed to other polypeptides, proteins, detectable moieties, labels, solid matrices, or carriers.

Amino acid residue linkers are usually at least one residue and can be 40 or more residues, more often 1 to 10 residues. Typical amino acid residues used for linking are glycine, tyrosine, cysteine, lysine, glutamic and aspartic acid, or the like. In addition, a subject polypeptide can differ by the sequence being modified by terminal-$NH_2$ acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

In some embodiments, the linker can be a flexible peptide linker that links the therapeutic peptide to other polypeptides, proteins, and/or molecules, such as detectable moieties, labels, solid matrices, or carriers. A flexible peptide linker can be about 20 or fewer amino acids in length. For example, a peptide linker can contain about 12 or fewer amino acid residues, e.g., 3, 4, 5, 6, 7, 8, 9, 10, 11, and 12. In some cases, a peptide linker comprises two or more of the following amino acids: glycine, serine, alanine, and threonine.

In some embodiments, a therapeutic agent comprising the therapeutic peptides described herein can be provided in the form of a conjugate protein or drug delivery construct includes at least a transport subdomain(s) or moiety(ies) (i.e., transport moieties) that is linked to the therapeutic peptide. The transport moieties can facilitate uptake of the therapeutic polypeptides into a mammalian (i.e., human or animal) tissue or cell (e.g., neural cell). The transport moieties can be covalently linked to the therapeutic polypeptides. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the therapeutic polypeptide. The transport moieties can also be linked to the therapeutic polypeptide with linking polypeptide described herein.

The transport moieties can be repeated more than once in the therapeutic agent. The repetition of a transport moiety may affect (e.g., increase) the uptake of the peptides and/or proteins by a desired cell. The transport moiety may also be located either at the amino-terminal region of therapeutic peptide or at its carboxy-terminal region or at both regions.

In one embodiment, the transport moiety can include at least one transport peptide sequence that allows the therapeutic polypeptide once linked to the transport moiety to penetrate into the cell by a receptor-independent mechanism. In one example, the transport peptide is a synthetic peptide that contains a Tat-mediated protein delivery sequence and at least one of SEQ ID NOs: 1-25 and 32. These peptides can have, respectively, the amino acid sequences of SEQ ID NOs: 33-58.

Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No. 2,301,157. Similarly, HIV Tat protein was shown to be able to cross cellular membranes.

In addition, the transport moiety(ies) can include polypeptides having a basic amino acid rich region covalently linked to an active agent moiety (e.g., intracellular domain-containing fragments inhibitor peptide). As used herein, the term "basic amino acid rich region" relates to a region of a protein with a high content of the basic amino acids such as arginine, histidine, asparagine, glutamine, lysine. A "basic amino acid rich region" may have, for example 15% or more of basic amino acid. In some instance, a "basic amino acid rich region" may have less than 15% of basic amino acids and still function as a transport agent region. In other instances, a basic amino acid region will have 30% or more of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of this application can function as a transport agent region.

In one embodiment, the therapeutic peptide described herein can be non-covalently linked to a transduction agent. An example of a non-covalently linked polypeptide transduction agent is the Chariot protein delivery system (See U.S. Pat. No. 6,841,535; *J Biol Chem* 274(35):24941-24946; and *Nature Biotec.* 19:1173-1176, all herein incorporated by reference in their entirety).

In other embodiments, the therapeutic peptides can be expressed in cells being treated using gene therapy to inhibit LAR family signaling or PTPσ signaling. The gene therapy can use a vector including a nucleotide encoding the therapeutic peptides. A "vector" (sometimes referred to as gene delivery or gene transfer "vehicle") refers to a macromolecule or complex of molecules comprising a polynucleotide to be delivered to the cell. The polynucleotide to be delivered may comprise a coding sequence of interest in gene therapy. Vectors include, for example, viral vectors (such as adenoviruses (Ad), adeno-associated viruses (AAV), and retroviruses), liposomes and other lipid-containing complexes, and other macromolecular complexes capable of mediating delivery of a polynucleotide to a target cell.

Vectors can also comprise other components or functionalities that further modulate gene delivery and/or gene expression, or that otherwise provide beneficial properties to the targeted cells. Such other components include, for example, components that influence binding or targeting to cells (including components that mediate cell-type or tissue-specific binding); components that influence uptake of the vector nucleic acid by the cell; components that influence localization of the polynucleotide within the cell after uptake (such as agents mediating nuclear localization); and components that influence expression of the polynucleotide. Such components also might include markers, such as detectable and/or selectable markers that can be used to detect or select for cells that have taken up and are expressing the nucleic acid delivered by the vector. Such components can be provided as a natural feature of the vector (such as the use of certain viral vectors which have components or functionalities mediating binding and uptake), or vectors can be modified to provide such functionalities.

Selectable markers can be positive, negative or bifunctional. Positive selectable markers allow selection for cells carrying the marker, whereas negative selectable markers allow cells carrying the marker to be selectively eliminated. A variety of such marker genes have been described, including bifunctional (i.e., positive/negative) markers (see, e.g., Lupton, S., WO 92/08796, published May 29, 1992; and Lupton, S., WO 94/28143, published Dec. 8, 1994). Such marker genes can provide an added measure of control that can be advantageous in gene therapy contexts. A large variety of such vectors are known in the art and are generally available.

Vectors for use herein include viral vectors, lipid based vectors and other non-viral vectors that are capable of delivering a nucleotide encoding the therapeutic peptides described herein to the target cells. The vector can be a targeted vector, especially a targeted vector that preferentially binds to neurons and. Viral vectors for use in the application can include those that exhibit low toxicity to a target cell and induce production of therapeutically useful quantities of the therapeutic peptide in a cell specific manner.

Examples of viral vectors are those derived from adenovirus (Ad) or adeno-associated virus (AAV). Both human and non-human viral vectors can be used and the recombinant viral vector can be replication-defective in humans. Where the vector is an adenovirus, the vector can comprise a polynucleotide having a promoter operably linked to a gene encoding the therapeutic peptides and is replication-defective in humans.

Other viral vectors that can be used herein include herpes simplex virus (HSV)-based vectors. HSV vectors deleted of one or more immediate early genes (IE) are advantageous because they are generally non-cytotoxic, persist in a state similar to latency in the target cell, and afford efficient target cell transduction. Recombinant HSV vectors can incorporate approximately 30 kb of heterologous nucleic acid.

Retroviruses, such as C-type retroviruses and lentiviruses, might also be used in the application. For example, retroviral vectors may be based on murine leukemia virus (MLV). See, e.g., Hu and Pathak, Pharmacol. Rev. 52:493-511, 2000 and Fong et al., Crit. Rev. Ther. Drug Carrier Syst. 17:1-60, 2000. MLV-based vectors may contain up to 8 kb of heterologous (therapeutic) DNA in place of the viral genes. The heterologous DNA may include a tissue-specific promoter and a nucleic acid encoding the therapeutic peptide. In methods of delivery to neural cells, it may also encode a ligand to a tissue specific receptor.

Additional retroviral vectors that might be used are replication-defective lentivirus-based vectors, including human immunodeficiency (HIV)-based vectors. See, e.g., Vigna and Naldini, J. Gene Med. 5:308-316, 2000 and Miyoshi et al., J. Virol. 72:8150-8157, 1998. Lentiviral vectors are advantageous in that they are capable of infecting both actively dividing and non-dividing cells.

Lentiviral vectors for use in the application may be derived from human and non-human (including SIV) lentiviruses. Examples of lentiviral vectors include nucleic acid sequences required for vector propagation as well as a tissue-specific promoter operably linked to a therapeutic peptide encoding nucleic acid. These former may include the viral LTRs, a primer binding site, a polypurine tract, att sites, and an encapsidation site.

In some aspects, a lentiviral vector can be employed. Lentiviruses have proven capable of transducing different types of CNS neurons (Azzouz et al., (2002) *J Neurosci*. 22: 10302-12) and may be used in some embodiments because of their large cloning capacity.

A lentiviral vector may be packaged into any lentiviral capsid. The substitution of one particle protein with another from a different virus is referred to as "pseudotyping". The vector capsid may contain viral envelope proteins from other viruses, including murine leukemia virus (MLV) or vesicular stomatitis virus (VSV). The use of the VSV G-protein yields a high vector titer and results in greater stability of the vector virus particles.

Alphavirus-based vectors, such as those made from semliki forest virus (SFV) and sindbis virus (SIN) might also be used in the application. Use of alphaviruses is described in Lundstrom, K., Intervirology 43:247-257, 2000 and Perri et al., Journal of Virology 74:9802-9807, 2000.

Recombinant, replication-defective alphavirus vectors are advantageous because they are capable of high-level heterologous (therapeutic) gene expression, and can infect a wide target cell range. Alphavirus replicons may be targeted to specific cell types by displaying on their virion surface a functional heterologous ligand or binding domain that would allow selective binding to target cells expressing a cognate binding partner. Alphavirus replicons may establish latency, and therefore long-term heterologous nucleic acid expression in a target cell. The replicons may also exhibit transient heterologous nucleic acid expression in the target cell.

In many of the viral vectors compatible with methods of the application, more than one promoter can be included in the vector to allow more than one heterologous gene to be expressed by the vector. Further, the vector can comprise a sequence, which encodes a signal peptide or other moiety, which facilitates expression of the therapeutic peptide from the target cell.

To combine advantageous properties of two viral vector systems, hybrid viral vectors may be used to deliver a nucleic acid encoding a therapeutic peptide to a target neuron, cell, or tissue. Standard techniques for the construction of hybrid vectors are well-known to those skilled in the art. Such techniques can be found, for example, in Sambrook, et al., In Molecular Cloning: A laboratory manual. Cold Spring Harbor, N.Y. or any number of laboratory manuals that discuss recombinant DNA technology. Double-stranded AAV genomes in adenoviral capsids containing a combination of AAV and adenoviral ITRs may be used to transduce cells. In another variation, an AAV vector may be placed into a "gutless", "helper-dependent" or "high-capacity" adenoviral vector. Adenovirus/AAV hybrid vectors are discussed in Lieber et al., J. Virol. 73:9314-9324, 1999. Retrovirus/adenovirus hybrid vectors are discussed in Zheng et al., Nature Biotechnol. 18:176-186, 2000. Retroviral genomes contained within an adenovirus may integrate within the target cell genome and effect stable gene expression.

Other nucleotide sequence elements, which facilitate expression of the therapeutic peptide and cloning of the vector are further contemplated. For example, the presence of enhancers upstream of the promoter or terminators downstream of the coding region, for example, can facilitate expression.

In accordance with another embodiment, a tissue-specific promoter can be fused to nucleotides encoding the therapeutic peptides described herein. By fusing such tissue specific promoter within the adenoviral construct, transgene expression is limited to a particular tissue. The efficacy of gene expression and degree of specificity provided by tissue specific promoters can be determined, using the recombinant adenoviral system of the present application. Neuron specific promoters, such as the platelet-derived growth factor β-chain (PDGF-β) promoter and vectors, are well known in the art.

In addition to viral vector-based methods, non-viral methods may also be used to introduce a nucleic acid encoding a therapeutic peptide into a target cell. A review of non-viral methods of gene delivery is provided in Nishikawa and Huang, Human Gene Ther. 12:861-870, 2001. An example of a non-viral gene delivery method according to the application employs plasmid DNA to introduce a nucleic acid encoding a therapeutic peptide into a cell. Plasmid-based gene delivery methods are generally known in the art.

Synthetic gene transfer molecules can be designed to form multimolecular aggregates with plasmid DNA. These aggregates can be designed to bind to a target cell. Cationic amphiphiles, including lipopolyamines and cationic lipids, may be used to provide receptor-independent nucleic acid transfer into target cells.

In addition, preformed cationic liposomes or cationic lipids may be mixed with plasmid DNA to generate cell-transfecting complexes. Methods involving cationic lipid formulations are reviewed in Feigner et al., Ann. N.Y. Acad. Sci. 772:126-139, 1995 and Lasic and Templeton, Adv. Drug Delivery Rev. 20:221-266, 1996. For gene delivery, DNA may also be coupled to an amphipathic cationic peptide (Fominaya et al., J. Gene Med. 2:455-464, 2000).

Methods that involve both viral and non-viral based components may be used according to the application. For example, an Epstein Barr virus (EBV)-based plasmid for therapeutic gene delivery is described in Cui et al., Gene Therapy 8:1508-1513, 2001. Additionally, a method involving a DNA/ligand/polycationic adjunct coupled to an adenovirus is described in Curiel, D. T., Nat. Immun 13:141-164, 1994.

Additionally, the nucleic acid encoding the therapeutic peptides can be introduced into the target cell by transfecting the target cells using electroporation techniques. Electroporation techniques are well known and can be used to facilitate transfection of cells using plasmid DNA.

Vectors that encode the expression of the therapeutic peptides can be delivered in vivo to the target cell in the form of an injectable preparation containing pharmaceutically acceptable carrier, such as saline, as necessary. Other pharmaceutical carriers, formulations and dosages can also be used in accordance with the present application.

Where the target cell includes a motor or sensory nerve cell being treated, such as motoneurons, the vector can be delivered by direct injection into or about the periphery of the neuron at an amount sufficient for the therapeutic peptide to be expressed to a degree, which allows for highly effective therapy. By injecting the vector directly into or about the periphery of the neuron, it is possible to target the vector transfection rather effectively, and to minimize loss of the recombinant vectors. This type of injection enables local transfection of a desired number of cells, especially at a site of injury, thereby maximizing therapeutic efficacy of gene transfer, and minimizing the possibility of an inflammatory response to viral proteins. Other methods of administering the vector to the target cells can be used and will depend on the specific vector employed.

The therapeutic peptide can be expressed for any suitable length of time within the target cell, including transient expression and stable, long-term expression. In one aspect of the application, the nucleic acid encoding the therapeutic peptide will be expressed in therapeutic amounts for a defined length of time effective to induce activity and growth of the transfected cells. In another aspect of the application, the nucleic acid encoding the therapeutic peptide will be expressed in therapeutic amounts for a defined length of time effective to increase survival rate of injured motoneurons, enhance regrowth across inhibitory central nervous system scar into re-implanted spinal roots, regenerate axons, decrease muscle atrophy, and/or promote motor functional recovery.

The therapeutic agents described herein may be modified (e.g., chemically modified). Such modification may be designed to facilitate manipulation or purification of the molecule, to increase solubility of the molecule, to facilitate administration, targeting to the desired location, to increase or decrease half life. A number of such modifications are known in the art and can be applied by the skilled practitioner.

In the methods of treatment disclosed herein, a therapeutically effective amount of the therapeutic agent is administered to the subject to treat the root avulsion injury and/or denervation induced muscle atrophy. In one embodiment, a formulation including the therapeutic agent can be administered to the subject in the period from the time of, for example, a root avulsion injury up to hours, days, and/or weeks after the injury has occurred, for example within 24 hours, several days, or weeks from the time of injury.

The therapeutic agents can be delivered to a subject by any suitable route, including, for example, local and/or systemic administration. Systemic administration can include, for example, parenteral administration, such as intramuscular, intravenous, intraarticular, intraarterial, intrathecal, subcutaneous, or intraperitoneal administration. The agent can also be administered orally, transdermally, topically, by inhalation (e.g., intrabronchial, intranasal, oral inhalation or intranasal drops) or rectally. In some embodiments, the therapeutic agent can be administered to the subject via intravenous administration using an infusion pump to deliver daily, weekly, or doses of the therapeutic agent.

Desirable features of local administration include achieving effective local concentrations of the therapeutic agent as well as avoiding adverse side effects from systemic administration of the therapeutic agent. In one embodiment, the therapeutic agent can be introduced directly into the root avulsion injury tissue.

Pharmaceutically acceptable formulations of the therapeutic agent can be suspended in aqueous vehicles and introduced through conventional hypodermic needles or using infusion pumps.

For injection, therapeutic agent can be formulated in liquid solutions, typically in physiologically compatible buffers such as Hank's solution or Ringer's solution. In addition, the therapeutic agent may be formulated in solid form and re-dissolved or suspended immediately prior to use. Lyophilized forms are also included. The injection can be, for example, in the form of a bolus injection or continuous infusion (such as using infusion pumps) of the therapeutic agent.

It will be appreciated that the amount, volume, concentration, and/or dosage of the therapeutic agent that is administered to any one animal or human depends on many factors, including the subject's size, body surface area, age, the particular composition to be administered, sex, time and route of administration, general health, and other drugs being administered concurrently. Specific variations of the above noted amounts, volumes, concentrations, and/or dosages of therapeutic agent can be readily be determined by one skilled in the art using the experimental methods described below.

In some embodiments, a therapeutic agent, such as a therapeutic peptide described herein, can be administered locally and/or systemically to a subject in need thereof at a dose or amount of about 0.1 µmol, about 1 µmol, about 5 µmol, about 10 µmol, or more; or about 0.0001 mg/kg, about 0.001 mg/kg, about 0.01 mg/kg, about 0.1 mg/kg, or about 1 mg/kg to about 5 mg/kg or 10 mg/kg of the subject being treated. The therapeutic agent can be administered daily, weekly, biweekly, monthly or less frequently until there is maximal innervation of the CSPG region.

In another embodiment, the therapeutic agent can be administered to a subject systemically by intravenous injection or locally at the site of injury, usually within about 24 hours, about 48 hours, about 100 hours, or about 200 hours or more of when an injury occurs (e.g., within about 6 hours, about 12 hours, or 24 hours, inclusive, of the time of the injury).

In other embodiments, a pharmaceutically acceptable formulation used to administer the therapeutic agent(s) can also be formulated to provide sustained delivery of the active compound to a subject. For example, the formulation may deliver the active compound for at least one, two, three, or four weeks, inclusive, following initial administration to the subject. For example, a subject to be treated in accordance with the method described herein can be treated with the therapeutic agent for at least 30 days (either by repeated administration or by use of a sustained delivery system, or both).

Approaches for sustained delivery include use of a polymeric capsule, a minipump to deliver the formulation, a biodegradable implant, or implanted transgenic autologous cells (see U.S. Pat. No. 6,214,622) Implantable infusion pump systems (e.g., INFUSAID pumps (Towanda, Pa.)); see Zierski et al., 1988; Kanoff, 1994) and osmotic pumps (sold by Alza Corporation) are available commercially and otherwise known in the art. Another mode of administration is via an implantable, externally programmable infusion pump. Infusion pump systems and reservoir systems are also described in, e.g., U.S. Pat. No. 5,368,562 and U.S. Pat. No. 4,731,058.

Vectors encoding the therapeutic peptides can often be administered less frequently than other types of therapeutics. For example, an effective amount of such a vector can range from about 0.01 mg/kg to about 5 or 10 mg/kg, inclusive; administered daily, weekly, biweekly, monthly or less frequently.

The ability to deliver or express the therapeutic peptides allows for cell activity modulation in a number of different cell types. The therapeutic peptides can be expressed, for example, in a motonerve cell via specific promoters.

It is further contemplated herein that enzymatically, for example, via chondroitinase: ChABC, modifying inhibitory extracellular matrices in the root avulsion injury site combined with administration of the therapeutic agents can maximize the sprouting capacity and functional impact of remaining nerve fibers. It is further contemplated that enhancing and/or bringing about much greater total fiber sprouting combined with enhancing the physiological output of the neurons themselves will act synergistically to enhance functional recovery. Therefore, in another embodiment, subjects can be administered chondroitinase ABC in addition to the therapeutic agents described herein to bring about an even more enhanced recovery than either treatment used alone. In some embodiments, bolus injections of ChABC into the vicinity of the root avulsion injury can promote innervation in a subject.

Example 1

In this Example, we show that manipulation of PTPσ by the therapeutic peptide, ISP (SEQ ID NO: 45), could help axons navigate scar tissue in the CNS-PNS transitional zone (TZ) and promote functional restoration after avulsion injury. Therefore, we avulsed rat cervical ventral roots (C5, C6, and C7) on one side, followed with re-implantation of only the C6 root for potential regeneration. We demonstrate that ISP administration remarkably promoted motor functional recovery. We also show that the treatment rescued motoneuron death, increased axon regeneration and resulted in healthier synapses between motoneurons and muscle fibers. Our results show PTPσ is a therapeutic target for root avulsion injury.

Methods

Animals

Adult female Sprague Dawley rats (2-3 months old, 200-300 g body weight) were ordered from Laboratory Animal Unit of the University of Hong Kong. The university Committee for Use of Live Animals in Teaching and Research approved all animal handling and operation procedures.

Avulsion-Replantation Injury Model

Animals were anaesthetized with a mixture of ketamine (80 mg per kg of body weight) and xylazine (8 mg per kg), by intraperitoneal injection. The right spine segments from the 4th cervical (C4) to the 2nd thoracic (T2) were exposed and dorsal laminectomy was performed on laminae C4 to C7. After the dura matter of this area was opened, the right side C5-C7 roots (both dorsal and ventral) were avulsed using a fine glass hook. The avulsed C5 and C7 roots together with their connected spinal nerves were cut and removed, leaving a gap between the nerves and spinal cord to prevent regrowth, whereas the ventral roots of C6 were reattached back to spinal cord for regeneration following procedures described previously. Any injury to the spinal cord was avoided.

Treatment and Grouping

ISP was designed and provided by Jerry Silver's lab 14. Started at 24 hours post surgery, all 26 injured rats were treated daily with ISP (500 µl at concentration of 5 µM, 11 µg/day) or vehicle (5% DMSO in saline, 500 µl), by subcutaneous injection near the injury site. For ISP administrated animals, 4 were randomly chosen for 6-week time point analysis, and the other 7 rats were kept for 12 weeks until the endpoint. For the vehicle group, 7 rats were utilized for the 6-week time point study and 8 rats for the 12-week time point.

Behavioral Test

The Terzis grooming test 21 (TGT) was conducted to evaluate motor function of the upper limb. Around 5 ml water was gradually sprayed onto the rat snout using a 5 ml syringe, which would elicit bilateral grooming responses by the upper limbs. A 0-5 rating criterion was applied for the ipsilateral upper limb: 0, no response; 1, flexion at elbow, not reaching the snout; 2, flexion reaching the snout; 3, reaching below the eyes; 4, reaching to the eyes; 5, reaching to the ears and beyond. 24 hours after surgery, TGT was performed and successful operations were indicated by a 0 score. From the 3th week post surgery until the endpoint, animals were subject to weekly TGT to monitor motor functional recovery. Data was shown as mean±s.e.m. Mann-Whitney U test was applied to perform statistical analysis.

Retrograde Labeling and Labeled Cell Number Counting 2 animals with the best and worst TGT performance were selected from each group at 6- and 12-week time point to perform retrograde labeling studies. Around 0.8 µl of Fluorogold (Fluorochrome, 6% in sterilized water) was injected slowly into the ipsilateral musculocutaneous nerve. 4 days after injection, labeled animals were perfused and fixed with 4% paraformaldehyde in phosphorylated buffer (PB). Spinal cord segments C5-T1 were collected and sectioned longitudinally, at a thickness of 25 µm. Section observation was carried out under microscopy (Zeiss Axiphot Microscope) with a 420 nm filter. Labeled cells in the C5-C7 segment were counted on every other section.

Assessment of Motoneuron Survival Rate

Fixed spinal cord segments C5-T1 were sectioned at a thickness of 25 µm. After antigen retrieval by incubation with 10 µg/ml proteinase K at 37° C. for 10 minutes, every third section was stained with a ChAT antibody (Millipore, 1:100) overnight at 4° C., followed with a secondary antibody (Invitrogen, 1:400, conjugated to AlexaFluor 568) incubation for 1.5 hour at room temperature. Numbers of ChAT positive motoneurons were counted separately for the ipsilateral and contralateral sides. The ratio of operated side number to that of intact side was computed. Data was displayed as mean±SD with chi-square test for statistical analysis.

Motor Endplate Assessment

Fixed ipsilateral and contralateral biceps (from 12-week time point rats) were sectioned longitudinally from the ventromedial to superficial side, at a thickness of 14 µm. Every 4th section was collected and 20 slides for each muscle were harvested to stain with σ-Bungarotoxin (σ-BTX, Invetrogen, Alexa Fluor 568 conjugated, 1:500) for 30 minutes. Numbers of motor endplates (MEP) on each section were counted. 10-15 MEPs from each section and 150-200 MEPs from one muscle were randomly chosen to take photos (MBF Nikon Microscope). MEP area was measured using image J. Area range was divided into six categories: from 0 to 500 µm2 separated by hundred and over 500 um2. For every biceps, numbers of MEPs falling into each category were counted and the proportion to the total number calculated. Data was expressed as mean±SD. One-way ANOVA was used for MEP number assessment, while student's t test was applied for MEP area distribution analysis.

Measuring Axon Number in Nerve Trunk

Two sites along the musculocutaneous nerve (distal to lateral cord and 2 mm proximal to biceps) were selected to assess numbers of motoneuron axons. Cross sections were cut at a thickness of 3 µm and immunostaining with ChAT was carried out as described in assessment of motoneuron survival rate. Number of ChAT positive axons was counted at each site. Data was demonstrated as mean±SD, and chi-square test was applied for statistical analysis.

Electron Microscopy

Two sites along the musculocutaneous nerve (distal to lateral cord and 2 mm proximal to biceps) were fixed overnight with a mixture of 2% PFA and 2.5% glutaraldehyde in 0.1M PB, followed with overnight fixation using 1% osmium tetroxide. The tissue was then dehydrated in graded ethanol (30%, 50%, 70%, 80%, 90%, 95% for 5 minutes each and 100% for 3 times in 30 minutes) and infiltrated with propylene oxide (PO) twice in 30 minutes, PO: Epon (1:1) for one hour and pure Epon overnight. After that, the nerve was embedded in Epon and polymerized at 60° C. for 72 hours. Semithin sections (0.5 μm) were cut by a microtome (Ultracut) using a glass knife before staining with 0.5% toluidine blue in 1% borax for 35 s. Light microscope (MBF Nikon Microscope) was used for observation and images were digitalized. Around 80 axons from each animal were randomly selected for area measurement using image J. Student's t test was applied for statistical analysis. Ultrathin sections of 90 nm thickness were stained with 3% uranyl acetate and 1% lead citrate and digital images captured by electron microscopy (TEM, Phillip model 208).

Hematoxylin and Eosin (H&E) Stain and Muscle Fiber Diameter Measurement

Cross and longitudinal sections of biceps were cut and processed for H&E staining. Briefly, sections were deparaffinized by toluene and rehydrated by degraded ethanol (100%, 100%, 95%, 95%, 75% ethanol, 2 minutes each). Nuclei were stained with Harris haematoxylin for 8 minutes, followed by differentiation with 0.3% acid alcohol. Cytoplasm was stained with eosin for 2 minutes. Sections were then subject to dehydration by graded ethanol (75%, 95%, 95% and 100%, 2 dips each; 100% for 2 minutes; 100% for 12 minutes). Light microscopy (MBF Nikon Microscope) was used for observation and images were digitalized. Around 200 muscle fibers from each biceps were randomly selected for diameter assessment. Z test was applied for statistical analysis.

Electromyography 12 weeks post surgery, 2 animals (1 scored 5 in Tersiz grooming test and the other graded 4) from both vehicle and ISP groups were selected for needle electromyography (EMG) analysis using an RM6240 multichannel signal process system (Chengdu Instrument Factory). Animals were anaesthetized and both left and right biceps were exposed, as well as their connected musculocutaneous nerves. The nerve was hooked onto a stimulation electrode, while two recording needle electrodes were inserted into the biceps at a 1-2 mm depth and with 5-7 mm distance. At least 4 different locations in one biceps were chosen to test the electrical activity of different motor units. Resting potential was recorded for around 2 minutes for each location, then different voltage stimulations (from 0 to 2 mV) were applied and responses recorded.

Data Analysis

All data was expressed as mean±SD, or mean±SEM (averaged Terzis grooming test score) or mean (axon area distribution in semithin sections). Type of hypothesis testing was described separately in each section. Student's t test was performed using Microsoft Excel. Other testing and all plotting were done using R. Significant difference was considered when P value was less than 0.05. All experiments were performed in a blinded fashion.

Results

Motor Functional Recovery is Enhanced by ISP Treatment

Functional recovery is the ultimate aim in any therapy for root avulsion injury. Therefore, we first asked whether ISP enabled better motor functional recovery after peripheral nerve avulsion injury/re-implantation surgery. The Terzis grooming test (TGT) evaluates motor function of the upper limb. A 0-5 rating criterion was utilized depending on the highest level to which the affected upper limb could reach. A zero score indicates loss of all function and 5 means complete grooming recovery. 24 hours after surgery, all animals were subjected to the Terzis grooming test and all scored 0, confirming successful surgery. Functional recovery started within 3 weeks in both ISP and vehicle treated, re-implanted groups. However, averaged TGT scores were remarkably increased by ISP treatment, and significant differences were observed at 3- and 6-weeks post surgery (p<0.05, Mann Whitney U test. FIG. 1A). At 6-weeks post surgery, 45.5% of ISP animals scored 5, while only 6.7% of vehicle achieved this level (FIGS. 1B and C). The proportion of animals that were scored 5 was always lower in the vehicle group throughout the testing period, even though they gradually recovered (FIGS. 1B and C). At 12-weeks post surgery only 50% of control rats scored 5 compared with 71.4% of ISP rats scoring 5 (FIGS. 1B and C).

Surviving and Regenerating Motoneurons were Increased after ISP Treatment

We further asked whether the functional improvements were associated with more motoneurons regenerating axons, especially into the distal peripheral nerve. Therefore, we performed retrograde labeling studies by injecting fluorogold into the musculocutaneous nerve and counted labeled cells in the ventral spinal cord. The 2 rats with the best and worst Terzis grooming test scores were chosen from each group, at both 6- and 12-weeks post surgery. As observed at the 6-week time point, ISP rats had, on average, 51% more cells labeled retrogradely from the muscle. As regeneration proceeded, labeled cells increased in both groups. However, differences between the two treatment groups in labeled cell numbers was further enlarged at 12-week post surgery, with 62% higher amounts of labeled cells in ISP animals (FIGS. 2A and B).

Next we asked whether the increased retrogradely labeled cell number could also be attributed to increased cell survival in addition to enhanced regeneration speed. Since it is essential to maintain avulsed motoneurons alive in order to achieve functional restoration, we investigated whether ISP promoted a higher survival rate of motoneurons. Choline acetyltransferase (ChAT), as a marker of motoneurons, is transiently down-regulated after root avulsion injury but returns to detectable levels at 4 weeks postoperatively. ChAT immunostaining has been used to quantify surviving motoneurons in long-term avulsion injury models. Therefore, we selected 5 best performing animals from each group and stained the 5th-7th cervical segments of the spinal cord with ChAT antibodies. The survival rate of motor neurons is expressed as the ratio of the number of ChAT positive motor neurons on the ipsilateral side to that in the contralateral side. At 12-weeks post surgery, a significantly higher survival rate was detected in ISP animals compared with vehicle rats (p<0.0001, Chi-square test) (FIGS. 2C and D). 61.2% of motoneurons remained alive in vehicle animals (which is consistent with our previous study of an avulsion-replantation model (62%)). By contrast, ISP enabled survival of 80.7% motor neurons.

Figure 2:
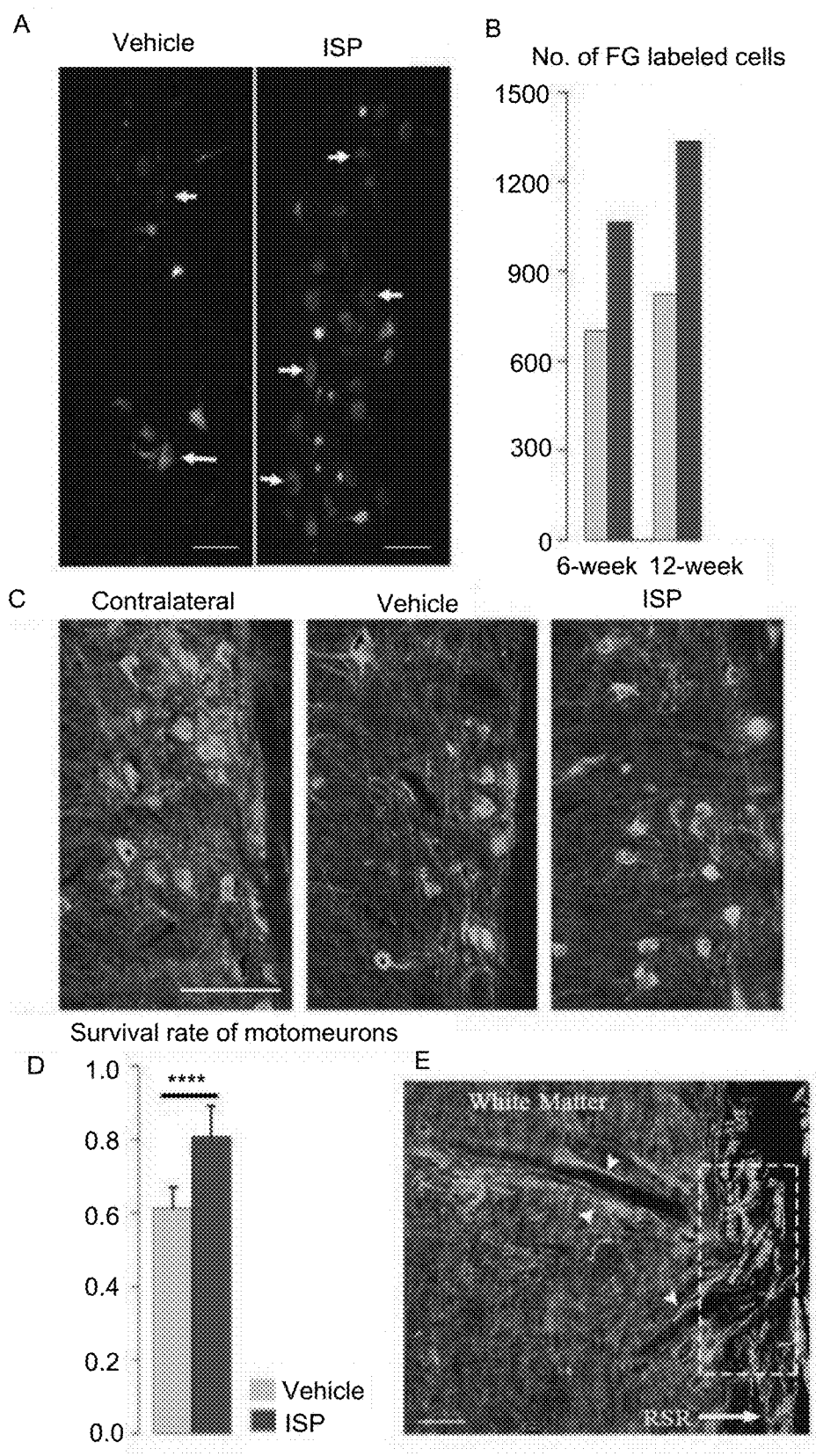
FIGS. 2A-E illustrate images and graphs showing motoneuron loss was reduced and regenerating cell number enlarged by ISP Intervention. (A) Retrograde labeled cells located in C6-C7 spinal cord segments after injecting fluorogold into musculocutaneous nerve. More labeled cells were observed in ISP treated animals. (B) Averaged Fluorogold labeled cell number at 6- and 12-week post surgery in both groups (n=2). At 6-week time point, 51.3% more cells were retrogradly labeled in ISP group than in vehicle rats, and this number was even enlarged to 61.5% at 12-week time point even though labeled cell number raised in both group. (C) Representative images showing spinal cord sections (C6 and C7 segments) stained with ChAT antibody. Motoneuron loss after avulsion/reimplantation was slowed down by ISP treatment. (D) Survival rate of motoneurons was calculated as the ratio of ChAT positive cell number in the ipsilateral spinal cord (C5-C7 segments) to that of the contralateral side. ISP treatment significantly increased survival rate of motoneurons from 61.2% in vehicle rats to 80.7% (data expressed as mean+SD, n=5, ****p<0.0001, chi-square test). (E) Newly formed axons in ISP animals (stained with ChAT, white arrowhead) navigated directly across spinal white matter and CNS-PNS TZ and formed physical connections (highlighted in dotted rectangle) with re-implanted spinal roots (RSR, white arrows). (Scale bars: 100 µm in (A) and (E), 200 µm in (C)).

Importantly, sections of the cord near the graft/host interface gave the impression that ISP treatment enabled newly formed axons to navigate directly across the CNS-PNS TZ and to elongate into the re-implanted root (FIG. 2E). It is inferred that modulation of the CSPG receptor PTPσ provided a pro-regenerative environment for axon elongation across the spinal cord and TZ after root avulsion.

Figure 3:
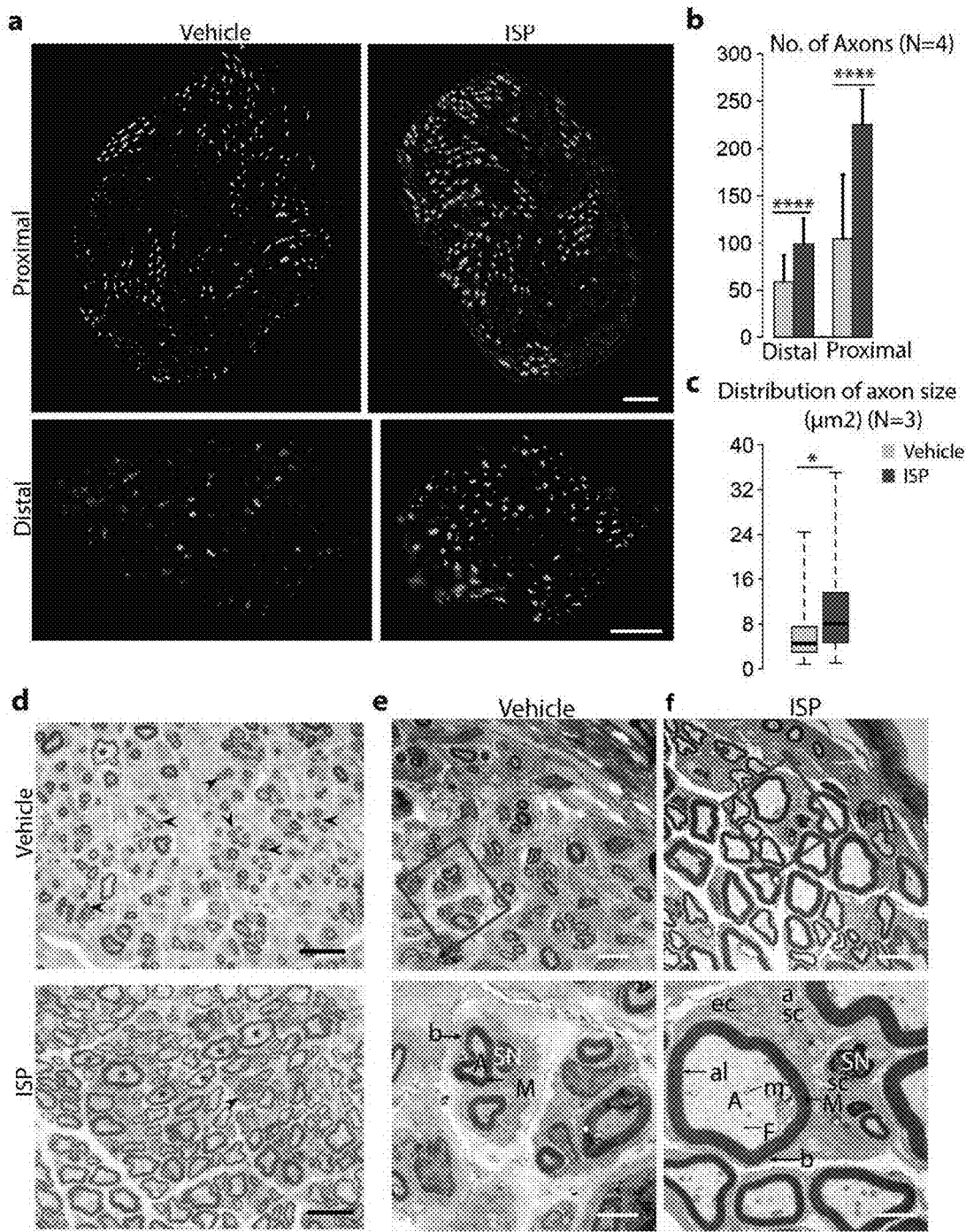
FIGS. 3A-F illustrate image and graphs showing numbers of motoneuron axons in the nerve trunk were increased and axon size enlarged in ISP rats. (A) Cross sections of proximal and distal musculocutaneous nerve (stained with ChAT). More axons were present at both sites in ISP animals. Vehicle treated rats showed not only less axon number, but also smaller size of axons with faint staining. (B) Numbers of axons at proximal and distal musculocutaneous nerve were significantly increased in ISP rats (****p<0.0001, oneway ANOVA). (C) Axonal size distribution of distal musculocutaneous nerve. Minimum, 1st quartile, median, 3rd quartile and maximum data points were marked in the plot. 76.7% vehicle axons were smaller than 8 µm², compared with only 50% of ISP axons in this size category. (D) Representative images of semithin sections taken from the distal musculocutaneous nerve show that ISP animals had more large-size axons while vehicle animals had more small-size axons. (Asterisks: remyelinated axons bigger than 5 µm²; arrowhead: axons smaller than 5 µm²) (E) Electron micrographs of distal musculocutaneous nerve. ISP axons not only demonstrated increased number and larger size but also were enwrapped by thicker myelin sheaths. Areas in red rectangle are illustrated with higher magnification in lower panel with a counterclockwise rotation of 35°. (A: myelinated axon, a: unmyelinated axon; M: myelin sheath; SN: Schwann cell nucleus; al: axolemma; (F): neurofilament; m: axon mitochondrion; b: basal lamina; sc: Schwann cell cytoplasm; ec: endonurial collagen fibers) (Scale bar: 50 µm in (a), 20 µm in (d), 5 µm in upper row of (e) and 2 µm in lower row).

ISP Facilitates More Axons with Bigger Sizes Extending into the Implanted Nerve Trunks We next confirmed quantitatively that ISP increased the number of motoneuron axons elongating into re-implanted injured nerves. Two sites along the musculocutaneous nerve were selected (proximal and distal end of the nerve) to count ChAT positive motoneuron axons. At both of the two sites, we detected twice the number of ChAT positive axons in ISP animals compared to the vehicle animals (FIGS. 3A and B. p<0.0001, chi-square test).

We further quantified axon size in the distal musculocutaneous nerve using semithin cross sections. About 23% of axons in the vehicle group were bigger than 8 µm², whereas over 50% of ISP treated axons fell into the same size range (FIGS. 3C and D. p<0.05, student's t test). Consistently, electron micrographs validated that ISP treatment enabled more axons with bigger sizes to extend through the distal musculocutaneous nerve. In addition, Schwann cells formed thicker myelin sheathes to insulate axons (FIG. 3E). Ultrastructural examination showed comprehensive regeneration in ISP animals, in that remyelinated axons with mitochondria and abundant neurofilaments were clearly ensheathed by Schwann cells and both basal lamina and endoneurium were well formed to pack single remyelinated axons. Groups of small unmyelinated axons were embedded in non-myelinating Schwann cells (FIG. 3E, lower panel).

ISP Animals Had Healthier Motor Endplates and Less Muscle Loss

Figure 4:
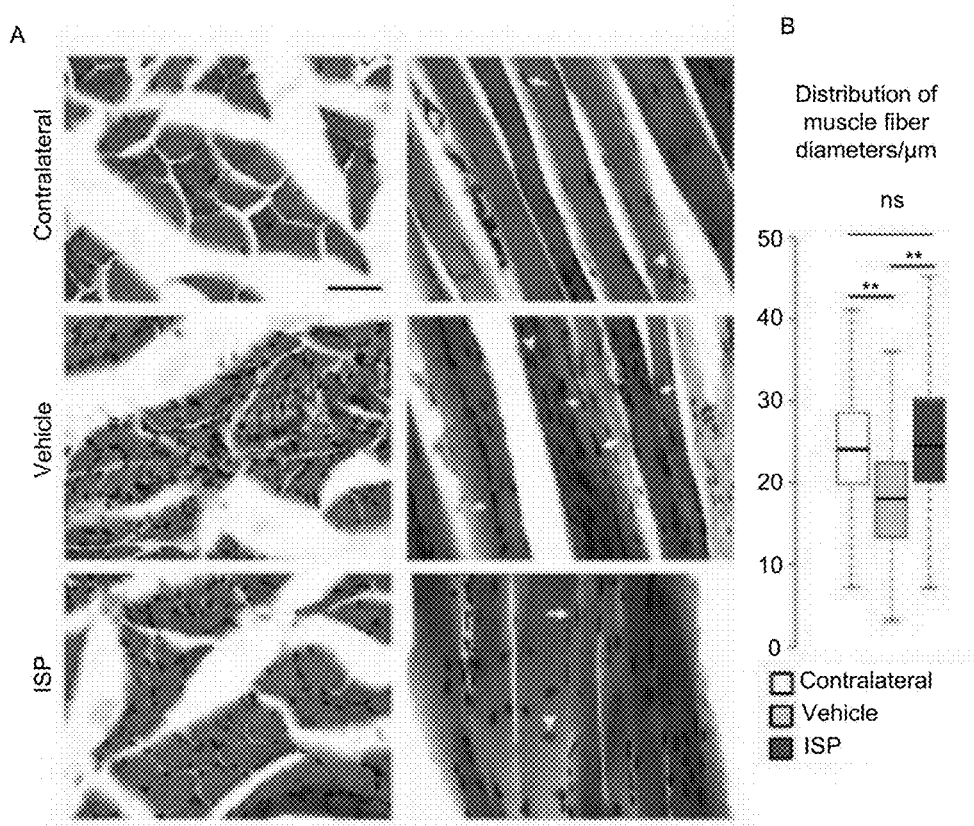
FIGS. 4A-B illustrate images and a graph showing muscle atrophy was reduced by ISP treatment. (A) Cross (left column) and longitudinal sections (right column) of biceps with H&E staining. Vehicle biceps exhibited more severe muscle atrophy, reflected by the shrunken sarcoplasm and presence of abundant fibroblast nuclei (white arrow). By contrast, ISP biceps with clear myocyte nucleus (white arrowhead) displayed less extent of fibrosis. (B) Distribution of muscle fiber diameter. Minimum, 1st quartile, median, 3rd quartile and maximum data points were plotted in the graph. 50% of contralateral and ISP muscle fibers had diameters bigger than 24 µm, while only 19% of vehicle muscle fibers showed the comparable diameters. (**p<0.01, ns: not significant, z test, n=6; Scale bar: 50 µm in (A)).
Figure 5:
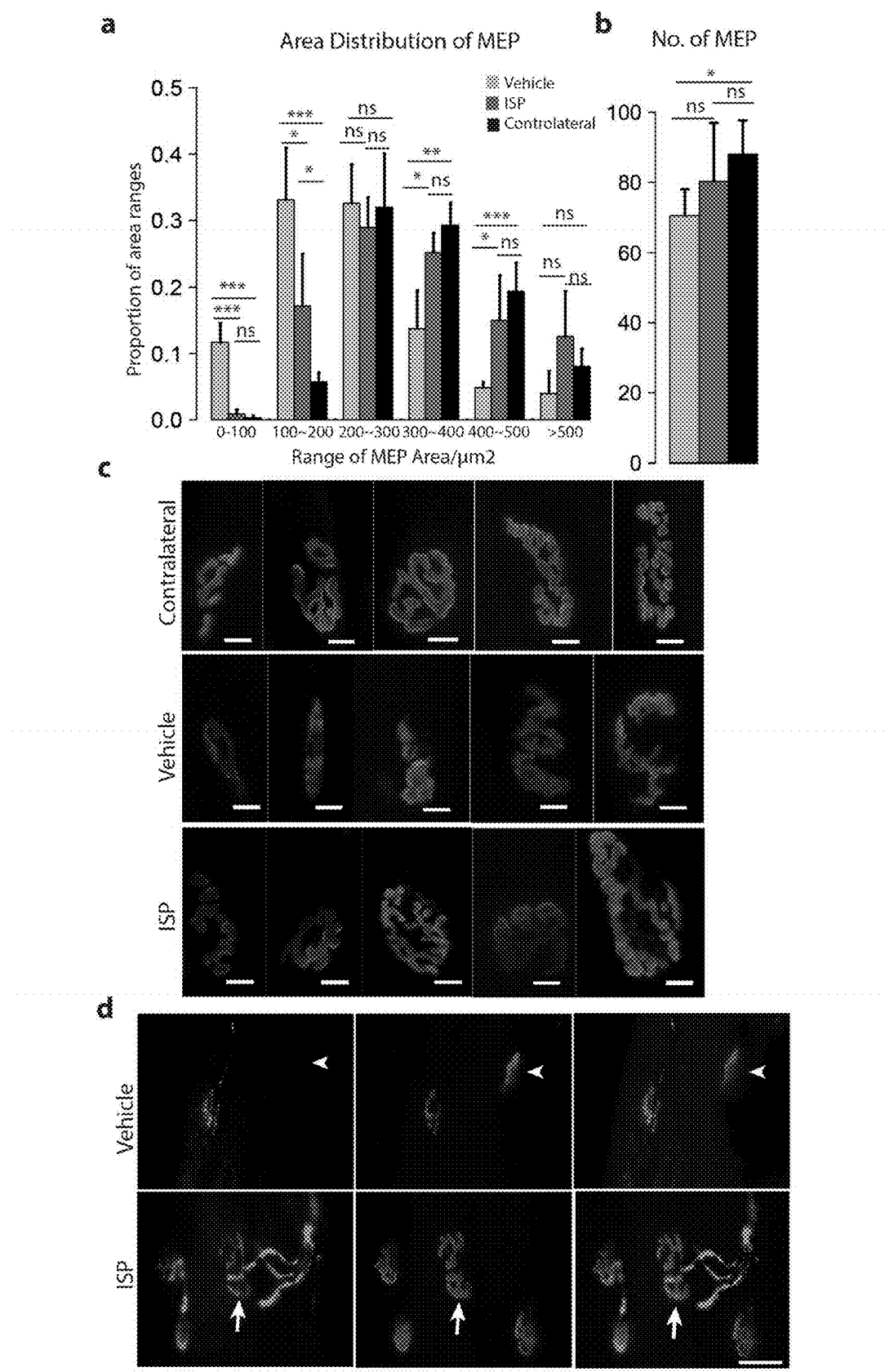
FIGS. 5A-D illustrate graphs and images showing ISP facilitated healthier neuromuscular junctions. (A) Area distribution of MEPs. The size distribution of ISP MEPs displayed higher similarity to normal contralateral MEPs, whereas vehicle MEPs had higher tendency to fall into the small size range. (*p<0.05, p<0.01, *p<0.001, **** p<0.0001, student's t test, n=4) (B) Averaged number of MEPs in biceps. Significantly smaller number was detected in vehicle biceps than that in the contralateral side, but no significant difference was found between ISP biceps and the un-operated side. (*p<0.05, One-way ANOVA, n=4) (C) Representative photos of motor endplates from contralateral, vehicle and ISP biceps. Vehicle MEPs not only have smaller sizes, but also show higher frequency to have ambiguous appearances and faint staining. (D) Illustrations showing motor endplates (stained with α-BTX, red, middle panel) with a lack of axon reinnervation (stained with ChAT, left panel). Poor or lack of reinnervation (white arrowhead, upper panel) lead to shrunken MEPs and vague morphology in vehicle animals. By contrast, ISP MEPs, with bigger sizes and clear shapes, showed nice costaining with axon terminals (white arrow, lower panel) (Scale bar: 10 µm in (C), 20 µm in (D))

We next evaluated recovery of the biceps, which is innervated only by the musculocutaneous nerve. Motoneuron axons exert a trophic effect on their controlled muscle fibers, via releasing neurotransmitter into the synaptic cleft and inducing contraction. Denervated muscle fibers develop morphological changes such as shrunken sarcoplasm and fibrosis. As reinnervation proceeds, instead of being scattered as in the contralateral biceps, muscle fibers become clustered in groups. Because some motoneurons die and fail to influence their target myocytes again, these muscle fibers tend to become reinnervated by adjacent axon sprouts, which consequently lead to fiber type grouping (FIG. 4A, lower left). Vehicle muscle fibers exhibited smaller cross sectional areas and higher amount of fibroblasts present within the endomysium. By contrast, ISP muscle fibers with clear myocyte nuclei showed higher morphological similarity to normal ones (FIG. 4A). Indeed, 50% of muscle fibers from both contralateral and ISP biceps had diameters bigger than 24 µm, whereas only 19% of vehicle muscle fibers displayed comparable sizes (FIG. 4B). The high similarity between contralateral (control) and ipsilateral ISP treated biceps was further confirmed by Motor endplate (MEP) assessment. MEPs are referred to as postsynaptic folds of neuromuscular junction between motoneurons and muscle fibers, in which acetylcholine receptors (AchRs) are located in high density. To assess the number and size changes of motor endplates, we stained the muscle sections with α-bungarotoxin (α-BTX), which specifically binds to AchRs. Numbers of MEPs were significantly decreased in vehicle biceps, compared with contralateral muscle, whereas numbers of MEPs in ISP biceps showed no obvious differences with normal ones (FIG. 5B). By randomly measuring areas of 150-200 MEPs from each biceps, we found that the area distribution of ISP MEPs showed higher similarity to normal ones, whereas Vehicle MEPs tended to fall into smaller categories (FIGS. 5A and C), indicating loss of AchR areas. Finally, vehicle motor endplates had a higher tendency to be faintly stained, suggesting lower density of AchRs that might result from diminished reinnervation (FIG. 5D, upper panel). Indeed, MEPs in ISP treated animals were well infiltrated by axon terminals, displayed bigger sizes and had clearer morphology (FIG. 5D, lower panel). Shrunken MEPs with fewer AchRs appeared in the biceps of vehicle treated animals which suggested that ISP promoted healthier neuromuscular junctions.

Improved Muscle Recovery was Associated with Electrophysiologically Healthier Motor Units Enhanced functional and morphological muscle recoveries were also reflected by marked improvement in the physiology of reinnervated motor units in ISP treated animals. Needle electromyography (EMG) detects extracellular electrical activity of muscle fibers and is applied to assess the health of motor units clinically. Denervated muscle fibers become supersensitive, which is reflected by the existence of spontaneous potentials during the resting state. These include fibrillation potentials and fasciculations. Fibrillations can be caused by hypersensitivity of muscle fibers to acetylchoine or partial depolarization and spontaneous oscillations of the membrane potential due to altered Na channel density and kinetics. Fibrillations persist for months after nerve lesion but they gradually disappear as reinnervation progresses. Clinically, the number of sites and the frequency of spontaneous potentials are adopted as rating criteria to assess the changes.

Figure 6:
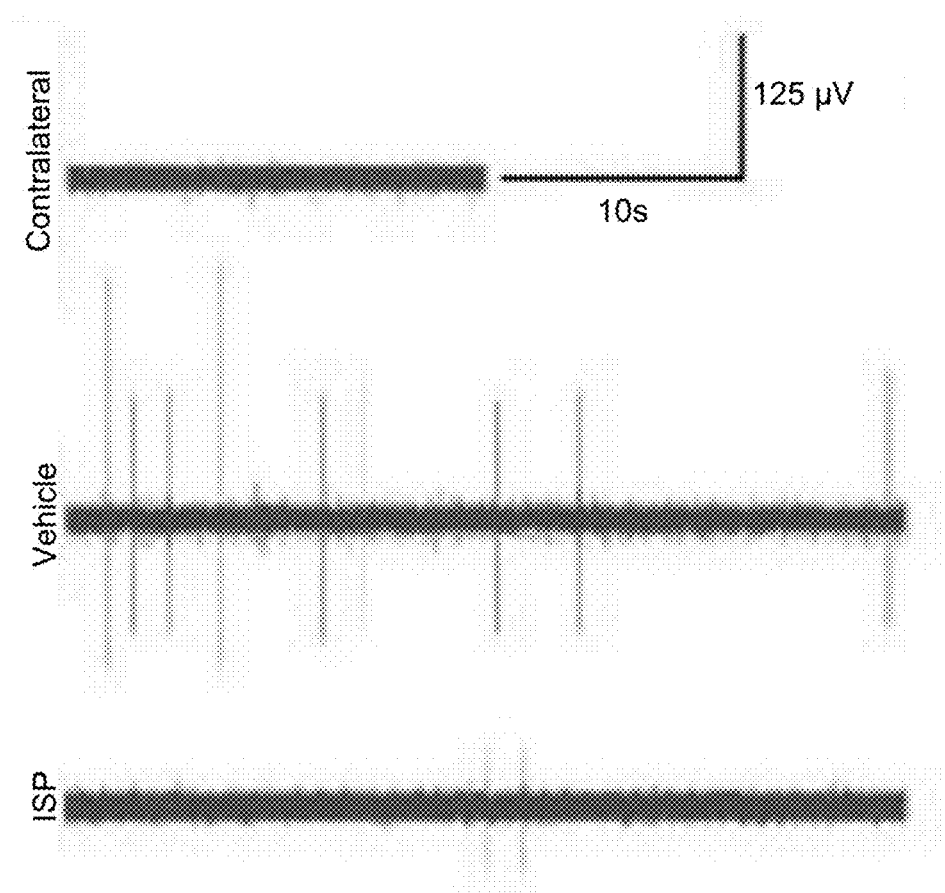
FIG. 6 illustrates traces of resting potentials showing reduced extent of electromyography abnormalities were recorded in the ISP treatment group. Fibrillations resulted from denervated motor units were not detected in contralateral biceps (upper panel) but appeared in both vehicle (middle panel) and ISP (lower panel) rats. A higher frequency was demonstrated in vehicle rats.

Animals with different TGT scores from the two treatment groups were subjected to needle EMG at 12-week postoperatively (Table 1). No spontaneous responses were detected in the biceps contralateral to the lesion side (FIG. 6, upper row). However, fibrillations appeared in the ipsilateral biceps of both vehicle (FIG. 6, middle row) and ISP treated (FIG. 6, lower row) animals. Resting potentials were recorded in 4-8 sites in each biceps and the number of spontaneous potentials counted. In line with the behavioral test, animals with better TGT performance had fewer sites displaying spontaneous potentials, and the frequency of the potentials decreased accordingly. (FIG. 6, Table 1).

TABLE 1

Spontaneous potential detected by needle EMG

| Treatment | TGT score | Sites tested | Sites with spontaneous potential | Frequency of spontaneous potential (Hz) |
|---|---|---|---|---|
| Vehicle | 4 | 5 | 5 | 0.272 |
|  | 5 | 4 | 1 | 0.109 |
| ISP | 4 | 5 | 3 | 0.210 |
|  | 5 | 8 | 2 | 0.069 |

Example 2

Optimization of Wedge Domain Peptides

We truncated ISP into two peptides, the first containing the N-terminal alpha helix and the 4 amino acid turn, and the second beginning with the turn and containing the C-terminal alpha helix. Both truncations were conjugated to Tat on the N-terminus. Only the first truncation allowed axons to traverse the gradient, while the C-terminal truncation was ineffective. (PRR)5-ISP, ISP conjugated to another known membrane penetrable sequence, demonstrated efficacy on par with ISP itself.

Methods

CSPG Gradient Crossing Assay

CSPG gradients were prepared as described previously (Tom, Steinmetz et al. 2004). Glass coverslips (1.6 mm, Fisher Sci, Pittsburgh, Pa.) coated with poly-L-lysine and nitrocellulose were spotted with a 2 µl solution of aggrecan (0.7 mg/ml) and laminin (5 µg/ml) in HBSS-CMF (4 spots/coverslip). After the spots were allowed to dry, the coverslips were incubated with laminin (5 µg/ml) in HBSS-CMF at 37° C. for 3 h. Dissociated DRG neurons were plated at a density of 1,000 cells/cm2 in Neurobasal-A supplemented with B27, Glutamax and penicillin/streptomycin and incubated for 5 d at 37° C. For peptide experiments, appropriate concentrations of peptide were added to the media at the time of plating. For ChABC experiments, 0.1 U/ml ChABC (Seikagaku, Tokyo, Japan) was added to coverslips for 2 h after the laminin bath prior to cell plating.

At 5 d, cultures were fixed in 4% paraformaldehyde in PBS for 30 min. After several rinses in PBS, the coverslips were incubated in blocking solution (5% normal goat serum or normal donkey serum, 0.1% BSA, and with or without 0.1% Triton X-100 in PBS) for 1 h at room temperature and then incubated overnight at 4° C. in primary antibody. Anti-βIII-tubulin (1:500; Sigma-Aldrich), anti-CS56 (1:500; Sigma-Aldrich), anti-PTPσ (1:100, R&D systems, Minneapolis, Minn. or 1:100, Abcam, Cambridge, Mass.) were used as primary antibodies. Coverslips were rinsed several times in PBS and then incubated in the appropriate secondary antibody (Molecular Probes, Eugene, Oreg.) overnight at 4° C. Coverslips were rinsed with PBS again, and mounted on glass slides in Citifluor (Ted Pella) mounting medium. Specimens were examined using a Leitz Orthoplan 2 fluorescence microscope.

Peptides were synthesized commercially with C-terminal amidation (Genscript, Piscataway, N.J.), and purity was assessed as >98% by mass spectrometry. Lyophilized peptides were dissolved in sterile water and stored at −80° C. until use. Peptide sequences are as follows:

```
                                                    (SEQ ID NO: 45)
ISP NH2-GRKKRRQRRRCDMAEHMERLKANDSLKLSQEYESI-NH2, (SEQ ID NO: 59)
TAT-NH2-GRKKRRQRRRC-NH2

(SEQ ID NO: 60)
PRR5-ISP-NH2-PRRPRRPRRPRRPRRDMAEHMERLKANDSLKLSQEY
ESI-NH2
```

Truncated Analogs

```
                                                    (SEQ ID NO: 61)
Truncated 1-NH2-GRKKRRQRRRCDMAEHMERLKANDS-NH2

(SEQ ID NO: 62)
Truncated 2-NH2-GRKKRRQRRRCANDSLKLSQEYESI-NH2
```

Quantification

The number of βIII-tubulin positive axons crossing the spot rim (visualized using the CS56 antigen) were counted and divided by the total number of neuronal cell bodies contained within each gradient. The results were normalized to ISP itself at 2.5 µM (set to 100%).

While this invention has been particularly shown and described with references to preferred embodiments thereof, it will be understood by those skilled in the art that various changes in form and details may be made therein without departing from the scope of the invention encompassed by the appended claims. All patents, publications and references cited in the foregoing specification are herein incorporated by reference in their entirety.

Having described the invention, we claim:

1. A method of treating root avulsion injury in a subject in need thereof, the method comprising:

administering to the subject a therapeutic agent that inhibits one or more of catalytic activity, signaling, and function of PTPσ, wherein the therapeutic agent comprises a therapeutic peptide, the therapeutic peptide including an amino acid sequence selected from the group consisting of SEQ ID NO: 32 and SEQ ID NO: 63.

2. The method of claim 1, the therapeutic agent comprising a therapeutic peptide consisting of an amino acid sequence selected from the group consisting of SEQ ID NO: 32 and SEQ ID NO: 63.

3. The method of claim 1, wherein the therapeutic agent includes a transport moiety that is linked to the therapeutic peptide and facilitates uptake of the therapeutic peptide by a nerve cell being treated.

4. The method of claim 3, wherein the transport moiety is an HIV Tat transport moiety.

5. The method of claim 3, wherein the therapeutic agent is administered systemically to the subject being treated.

6. The method of claim 1, further comprising connecting an avulsed end in a peripheral nerve to a portion of the central nervous system.

7. The method of claim 1, wherein the therapeutic agent is administered at an amount effective to increase survival rate of injured motoneurons, enhance regrowth across inhibitory central nervous system scar into re-implanted spinal roots, regenerate axons, decrease muscle atrophy, and/or promote motor functional recovery.

* * * * *